US008647310B2

(12) United States Patent
Fangrow, Jr. et al.

(10) Patent No.: US 8,647,310 B2
(45) Date of Patent: Feb. 11, 2014

(54) MEDICAL CONNECTOR WITH CLOSEABLE LUER CONNECTOR

(75) Inventors: Thomas F. Fangrow, Jr., Mission Viejo, CA (US); Bruce Hubrecht, Canyon Lake, CA (US)

(73) Assignee: ICU Medical, Inc., San Clemente, CA (US)

( * ) Notice: Subject to any disclaimer, the term of this patent is extended or adjusted under 35 U.S.C. 154(b) by 194 days.

(21) Appl. No.: 13/100,508

(22) Filed: May 4, 2011

(65) Prior Publication Data

US 2011/0276035 A1 Nov. 10, 2011

Related U.S. Application Data

(60) Provisional application No. 61/332,103, filed on May 6, 2010.

(51) Int. Cl.
*A61M 5/315* (2006.01)

(52) U.S. Cl.
USPC ........................................ 604/236; 251/149.2

(58) Field of Classification Search
USPC ............. 604/533–537, 236; 251/149.5, 149.2
See application file for complete search history.

(56) References Cited

U.S. PATENT DOCUMENTS

| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |

(Continued)

FOREIGN PATENT DOCUMENTS

| EP | 0 791 371 A1 | 8/1997 |
| EP | 1 946 792 | 7/2008 |

(Continued)

OTHER PUBLICATIONS

U.S. Appl. No. 10/584,920, filed Dec. 28, 2006, including its prosecution history.

(Continued)

*Primary Examiner* — Kevin Sirmons
*Assistant Examiner* — Deanna K Hall
(74) *Attorney, Agent, or Firm* — Knobbe Martens Olson & Bear LLP

(57) ABSTRACT

Some embodiments relate to a luer connector comprising a housing having a hollow bore therethrough, a first end, and a second end, a male luer tip supported by the housing configured to rotate with respect to the housing, the luer tip having a first open end and a passageway through the luer tip in fluid communication with the first open end, and a substantially rigid internal member extending into the passageway of the luer tip toward the first open end of the luer tip. In some embodiments, at least one of the luer tip and the internal member can be axially moveable between a first closed position and a second open position relative to the other of the luer tip and the internal member. Further, the luer tip and the internal member can cooperate such that rotation of the luer tip in a first direction relative to the housing increases an axial displacement between the first open end of the luer tip and an end portion of the internal member.

18 Claims, 16 Drawing Sheets

(56) References Cited

U.S. PATENT DOCUMENTS

| | | |
|---|---|---|
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,457,749 A | 7/1984 | Bellotti et al. |
| 4,511,359 A | 4/1985 | Vaillancourt |
| 4,538,836 A | 9/1985 | Kruetten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,700,744 A | 10/1987 | Rutter et al. |
| 4,723,603 A | 2/1988 | Plummer |
| 4,728,075 A | 3/1988 | Paradis |
| 4,745,950 A | 5/1988 | Mathieu |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,950,260 A | 8/1990 | Bonaldo |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,735,826 A | 4/1998 | Richmond |
| 5,738,144 A | 4/1998 | Rogers |
| 5,749,861 A | 5/1998 | Guala et al. |
| RE35,841 E | 7/1998 | Frank et al. |

(56) References Cited

U.S. PATENT DOCUMENTS

| | | | |
|---|---|---|---|
| 5,782,816 A | 7/1998 | Werschmidt et al. | |
| 5,785,693 A | 7/1998 | Haining | |
| 5,806,831 A | 9/1998 | Paradis | |
| 5,814,024 A | 9/1998 | Thompson et al. | |
| 5,820,601 A | 10/1998 | Mayer | |
| 5,839,715 A | 11/1998 | Leinsing | |
| 5,848,994 A | 12/1998 | Richmond | |
| 5,947,954 A | 9/1999 | Bonaldo | |
| 6,029,946 A | 2/2000 | Doyle | |
| 6,036,171 A | 3/2000 | Weinheimer et al. | |
| 6,050,978 A | 4/2000 | Orr et al. | |
| 6,063,062 A | 5/2000 | Paradis | |
| 6,068,011 A | 5/2000 | Paradis | |
| 6,068,617 A | 5/2000 | Richmond | |
| 6,079,432 A | 6/2000 | Paradis | |
| 6,106,502 A | 8/2000 | Richmond | |
| 6,113,068 A | 9/2000 | Ryan | |
| 6,142,446 A | 11/2000 | Leinsing | |
| 6,152,913 A | 11/2000 | Feith et al. | |
| 6,168,137 B1 | 1/2001 | Paradis | |
| 6,171,287 B1 | 1/2001 | Lynn et al. | |
| 6,189,859 B1 | 2/2001 | Rohrbough et al. | |
| 6,206,860 B1 | 3/2001 | Richmond | |
| 6,224,578 B1 | 5/2001 | Davis et al. | |
| 6,242,393 B1 | 6/2001 | Ishida et al. | |
| 6,245,048 B1 | 6/2001 | Fangrow et al. | |
| 6,290,206 B1 | 9/2001 | Doyle | |
| 6,299,132 B1 | 10/2001 | Weinheimer et al. | |
| 6,428,520 B1 | 8/2002 | Lopez | |
| 6,431,219 B1 | 8/2002 | Redler et al. | |
| 6,485,472 B1 | 11/2002 | Richmond | |
| 6,499,719 B1 | 12/2002 | Clancy et al. | |
| 6,508,792 B2 | 1/2003 | Szames et al. | |
| 6,508,807 B1 | 1/2003 | Peters | |
| 6,541,802 B2 | 4/2003 | Doyle | |
| 6,543,745 B1 | 4/2003 | Enerson | |
| 6,581,906 B2 | 6/2003 | Pott et al. | |
| 6,585,229 B2 | 7/2003 | Cote et al. | |
| 6,595,964 B2 | 7/2003 | Finley et al. | |
| 6,595,981 B2 | 7/2003 | Huet | |
| 6,609,696 B2 | 8/2003 | Enerson | |
| 6,666,852 B2 | 12/2003 | Niedospial, Jr. | |
| 6,695,817 B1 | 2/2004 | Fangrow | |
| 6,745,998 B2 | 6/2004 | Doyle | |
| 6,840,501 B2 | 1/2005 | Doyle | |
| 6,869,426 B2 | 3/2005 | Ganem | |
| 6,875,205 B2 | 4/2005 | Leinsing | |
| 6,899,315 B2 | 5/2005 | Mailville et al. | |
| 6,955,669 B2 | 10/2005 | Curutcharry | |
| 6,964,406 B2 | 11/2005 | Doyle | |
| 7,004,934 B2 | 2/2006 | Vaillancourt | |
| 7,037,302 B2 | 5/2006 | Vaillancourt | |
| 7,040,598 B2 | 5/2006 | Raybuck | |
| 7,044,441 B2 | 5/2006 | Doyle | |
| 7,100,891 B2 | 9/2006 | Doyle | |
| 7,125,396 B2 | 10/2006 | Leinsing et al. | |
| 7,140,592 B2 | 11/2006 | Phillips | |
| 7,182,313 B2 | 2/2007 | Doyle | |
| 7,195,228 B2 | 3/2007 | Tiberghien et al. | |
| 7,244,249 B2 | 7/2007 | Leinsing et al. | |
| 7,306,197 B2 | 12/2007 | Parrino et al. | |
| 7,306,198 B2 | 12/2007 | Doyle | |
| 7,306,566 B2 | 12/2007 | Raybuck | |
| 7,347,458 B2 | 3/2008 | Rome et al. | |
| 7,350,764 B2 | 4/2008 | Raybuck | |
| 7,361,164 B2 | 4/2008 | Simpson et al. | |
| 7,497,484 B2 | 3/2009 | Ziman | |
| 7,559,530 B2 | 7/2009 | Korogi et al. | |
| 7,588,563 B2 | 9/2009 | Guala | |
| 7,645,274 B2 | 1/2010 | Whitley | |
| 7,651,481 B2 | 1/2010 | Raybuck | |
| 7,666,170 B2 | 2/2010 | Guala | |
| 7,758,566 B2 | 7/2010 | Simpson et al. | |
| 7,766,304 B2 | 8/2010 | Phillips | |
| 7,766,897 B2 | 8/2010 | Ramsey et al. | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,837,658 B2 * | 11/2010 | Cote et al. | 604/236 |
| 7,857,805 B2 | 12/2010 | Raines | |
| 7,976,532 B2 | 7/2011 | Kitani et al. | |
| 7,998,134 B2 | 8/2011 | Fangrow et al. | |
| 8,066,692 B2 | 11/2011 | Simpson et al. | |
| 8,211,069 B2 | 7/2012 | Fangrow, Jr. | |
| 8,262,628 B2 | 9/2012 | Fangrow, Jr. | |
| 2001/0029355 A1 | 10/2001 | Szames et al. | |
| 2002/0066715 A1 | 6/2002 | Niedospial, Jr. | |
| 2003/0060804 A1 | 3/2003 | Vaillancourt | |
| 2003/0066978 A1 | 4/2003 | Enerson | |
| 2003/0111623 A1 | 6/2003 | Enerson | |
| 2003/0136932 A1 | 7/2003 | Doyle | |
| 2003/0208165 A1 | 11/2003 | Christensen et al. | |
| 2004/0124388 A1 | 7/2004 | Kiehne | |
| 2004/0124389 A1 | 7/2004 | Phillips | |
| 2005/0015075 A1 | 1/2005 | Wright et al. | |
| 2005/0124942 A1 | 6/2005 | Richmond | |
| 2005/0212292 A1 | 9/2005 | Parrino et al. | |
| 2005/0228362 A1 | 10/2005 | Vaillancourt | |
| 2005/0245872 A1 | 11/2005 | Simpson et al. | |
| 2006/0058734 A1 | 3/2006 | Phillips | |
| 2006/0129109 A1 | 6/2006 | Shaw et al. | |
| 2006/0142730 A1 | 6/2006 | Proulx et al. | |
| 2006/0142735 A1 | 6/2006 | Whitley | |
| 2006/0149213 A1 | 7/2006 | Raybuck | |
| 2006/0157984 A1 | 7/2006 | Rome et al. | |
| 2006/0161115 A1 | 7/2006 | Fangrow | |
| 2006/0192164 A1 | 8/2006 | Korogi et al. | |
| 2006/0202146 A1 | 9/2006 | Doyle | |
| 2006/0253084 A1 | 11/2006 | Nordgren | |
| 2007/0073270 A1 | 3/2007 | Christensen et al. | |
| 2007/0088292 A1 | 4/2007 | Fangrow | |
| 2007/0088293 A1 | 4/2007 | Fangrow | |
| 2007/0088294 A1 | 4/2007 | Fangrow | |
| 2007/0088324 A1 * | 4/2007 | Fangrow, Jr. | 604/533 |
| 2007/0088327 A1 | 4/2007 | Guala | |
| 2007/0179453 A1 | 8/2007 | Lim et al. | |
| 2008/0103485 A1 | 5/2008 | Kruger | |
| 2008/0190485 A1 | 8/2008 | Guala | |
| 2010/0174242 A1 | 7/2010 | Anderson et al. | |
| 2010/0249723 A1 | 9/2010 | Fangrow, Jr. | |
| 2011/0046572 A1 | 2/2011 | Fangrow | |
| 2011/0306931 A1 | 12/2011 | Kamen et al. | |
| 2012/0041391 A1 | 2/2012 | Fangrow et al. | |
| 2012/0089101 A1 | 4/2012 | Carlyon et al. | |
| 2012/0271244 A1 | 10/2012 | Simpson et al. | |
| 2012/0330247 A1 | 12/2012 | Fangrow, Jr. | |
| 2013/0150806 A1 | 6/2013 | Fangrow, Jr. | |
| 2013/0231616 A1 | 9/2013 | Fangrow, Jr. | |

FOREIGN PATENT DOCUMENTS

| | | |
|---|---|---|
| GB | 2 116 277 | 9/1983 |
| GB | 2 118 440 | 11/1983 |
| GB | 2 353 078 | 2/2001 |
| JP | 11-311234 | 11/1999 |
| JP | 2013-525071 | 6/2013 |
| WO | WO 01/03756 | 1/2001 |
| WO | WO 2004/060474 A1 | 7/2004 |
| WO | WO 2004/082756 | 9/2004 |
| WO | WO 2006/076656 | 7/2006 |
| WO | WO 2006/088858 | 8/2006 |
| WO | WO 2006/124756 | 11/2006 |
| WO | WO 2013/036854 | 3/2013 |

OTHER PUBLICATIONS

U.S. Appl. No. 11/417,604, filed May 3, 2006, including its prosecution history.
U.S. Appl. No. 11/417,836, filed May 3, 2006, including its prosecution history.
U.S. Appl. No. 11/482,176, filed Jul. 6, 2006, including its prosecution history.
U.S. Appl. No. 12/117,568, filed May 8, 2008, including its prosecution history.

(56) References Cited

OTHER PUBLICATIONS

U.S. Appl. No. 12/789,255, filed May 27, 2010, including its prosecution history.
U.S. Appl. No. 12/893,789, filed Sep. 29, 2010, including its prosecution history.
U.S. Appl. No. 11/417,923, filed May 3, 2006, and its prosecution history, Gustus et al.
U.S. Appl. No. 11/417,671, filed May 3, 2006, and its prosecution history, Gustus et al.
U.S. Appl. No. 11/417,648, filed May 3, 2006, and its prosecution history, Gustus et al.
U.S. Appl. No. 11/417,909, filed May 3, 2006, and its prosecution history, Gustus et al.
U.S. Appl. No. 11/417,882, filed May 3, 2006, and its prosecution history, Gustus et al.
U.S. Appl. No. 11/417,556, filed May 3, 2006, including its prosecution history.
U.S. Appl. No. 11/417,567, filed May 3, 2006, including its prosecution history.
U.S. Appl. No. 11/418,155, filed May 3, 2006, including its prosecution history.
U.S. Appl. No. 12/651,283, filed Dec. 17, 2009, including its prosecution history.
U.S. Appl. No. 13/210,261, filed Aug. 15, 2011, including its prosecution history.
U.S. Appl. No. 13/305,663, filed Nov. 28, 2011, including its prosecution history.
U.S. Appl. No. 12/534,663, filed Jun. 27, 2012, including its prosecution history.
U.S. Appl. No. 13/606,520, filed Sep. 7, 2012, including its prosecution history.
U.S. Appl. No. 13/865,147, filed Apr. 17, 2013, including its prosecution history.
International Search Report and Written Opinion re PCT App. No. PCT/US2011/034854, mailed Mar. 28, 2012, in 19 pages.
International Preliminary Report on Patentability re PCT App. No. PCT/US2011/034854, issued Nov. 6, 2012, in 12 pages.

\* cited by examiner

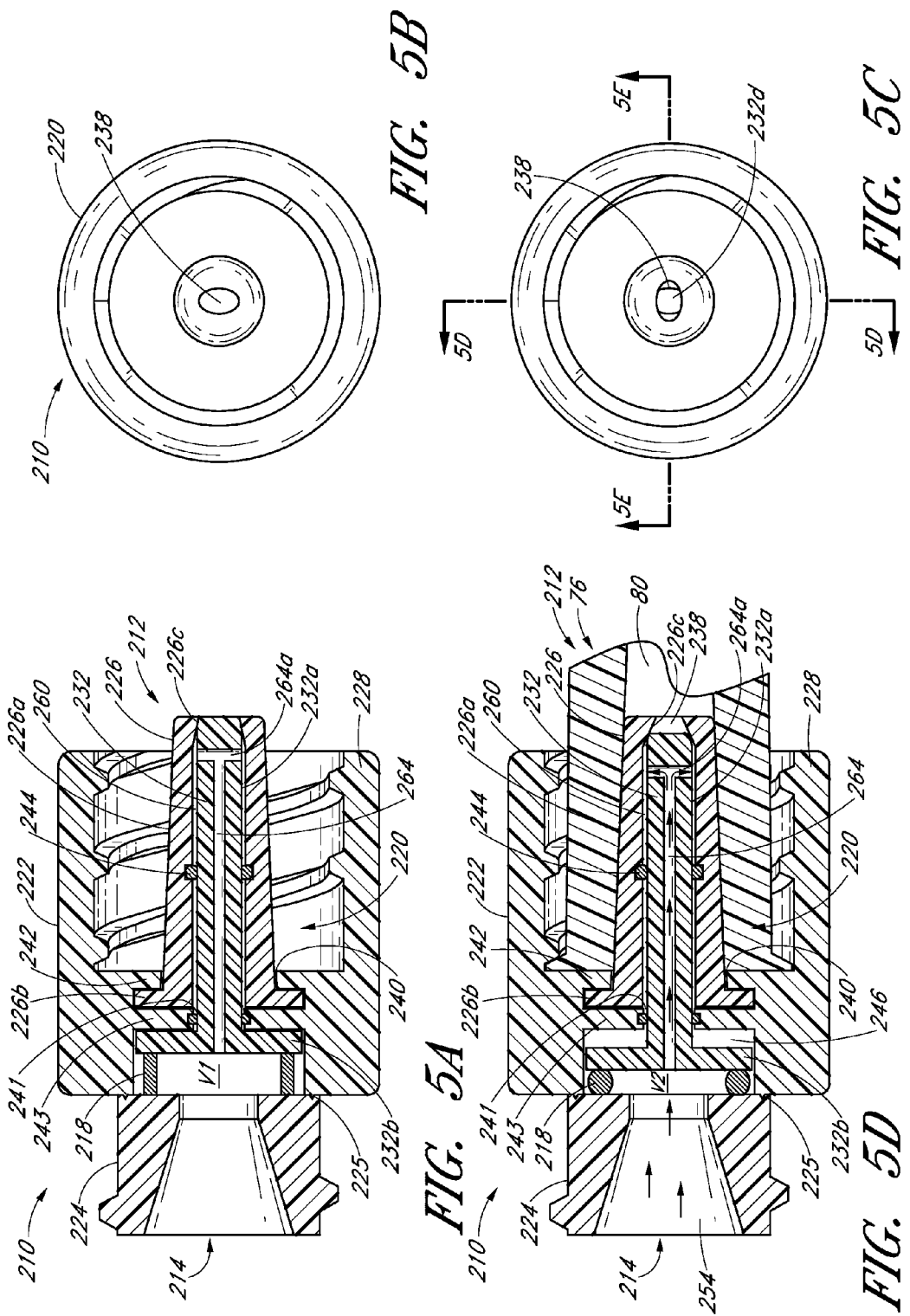

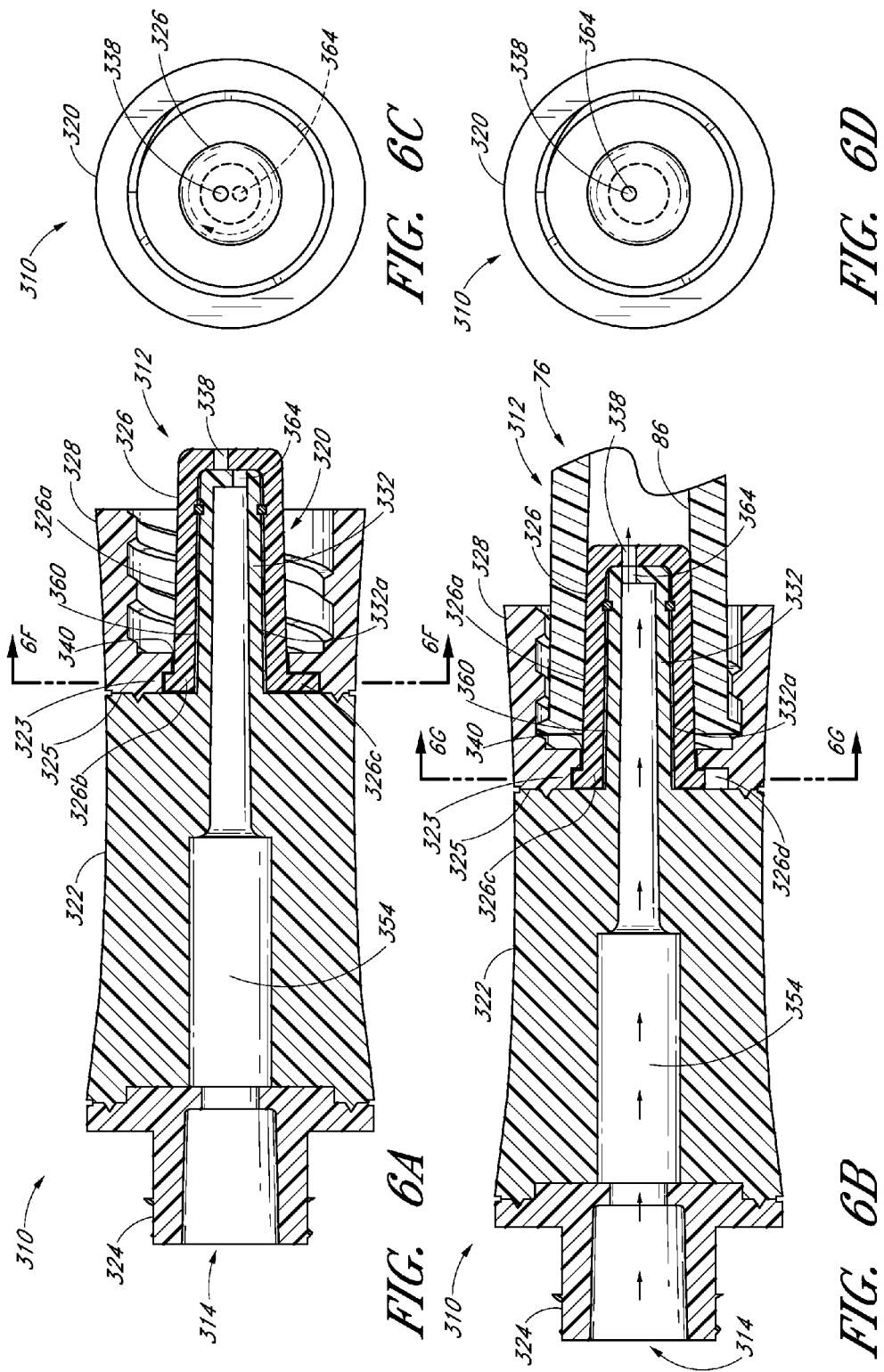

MEDICAL CONNECTOR WITH CLOSEABLE LUER CONNECTOR

PRIORITY INFORMATION AND INCORPORATION BY REFERENCE

This application claims priority benefit of U.S. Provisional Application 61/332,103 (titled "Medical Connector With Closeable Luer Connector"), filed May 6, 2010, which application is hereby incorporated by reference in its entirety as if fully set forth herein. The benefit of priority is claimed under the appropriate legal basis including, without limitation, under 35 U.S.C. §119(e).

BACKGROUND OF THE DISCLOSURE

1. Field of the Disclosure

Embodiments of this disclosure relate generally to medical connectors through which fluids flow, and in particular, to medical connectors with male luers.

2. Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged. In order to maintain a barrier to bacteria, debris, and fluid leakage, female connectors often have been provided with closures, such as septa, flexible seals, or other impediments, at their mating ends. When a male luer connector is engaged with the female connector, the closure of the female connector is temporarily opened, pierced, or moved to allow fluid to flow between the two connectors. Male connectors typically employ needles or luers to open, pierce, or move the closure on the female connectors.

In many systems, only the female connectors are automatically blocked from the external environment when disengaged. Male luer connectors are generally not provided with automatic closing mechanisms. Male luer connectors sometimes employ additional components, such as caps, to stop the flow of fluid and impede the entry of bacteria and debris. Because such closure mechanisms are not automatic (or not used at all), male luer connectors are sometimes left unsealed, allowing fluid to drip out. This may increase the risk of unsanitary conditions inside and outside of the fluid transfer system. In addition, in some medical applications such as certain chemotherapy treatments, the fluids in the tubing and connectors can be harmful if released.

Moreover, in the busy environment of hospitals and other medical settings, health care providers must often quickly manipulate multiple medical implements with one hand, making it difficult to retrieve male luer caps and rapidly attach them upon disengagement of male connectors. In addition, male luer connectors are often employed at the downstream end of gravity-fed fluid sources such as IV bags. When the connectors and tubing are initially connected to such sources, they are generally empty (e.g., filled with air) and must be primed with fluid before they can be connected to a patient. During the priming procedure, fluid is allowed to flow from the upstream end of the tubing toward the male luer connector on the downstream end.

As the fluid flows through the tubing, the air in the tubing escapes through the male connector on the downstream end into the environment. Once the fluid itself reaches the male connector, it can also escape and spill out. Because male luer connectors do not usually close automatically after priming, the male luer often drips out a small amount of fluid as the male connector is rapidly moved into mating engagement with a female connector. For this reason, the male luer is generally held over a sink or trash can at the end of the priming procedure to contain the dripping fluid.

SUMMARY OF SOME EXEMPLIFYING EMBODIMENTS

Disclosed are various embodiments of medical connectors with closeable male luers. It is contemplated that one or more of the features of the various embodiments disclosed herein are combinable with one or more features of other embodiments to form additional embodiments. Such combinations are within the scope of this disclosure. In some embodiments, closeable male luer connectors automatically open when engaged with a female connector and automatically close when disengaged from such connector or easily can be mechanically opened or closed to minimize or eliminate dripping during priming and other procedures and to improve the barrier of the fluid transfer system against bacteria and other debris. In some embodiments, a closable male luer can be mechanically opened by a user without disrupting the mechanical connection between connectors (e.g., such as by unscrewing connections between housings) so as to minimize or eliminate dripping during priming and other procedures and to improve the barrier of the fluid system against bacteria and other debris, as well as to allow the user to more carefully control the timing of the opening of the closable male luer.

In some embodiments, a male luer connector has a main housing with first and second ends. The first end of the housing can comprise a male luer and a shroud surrounding at least a portion of the male luer. The shroud can include screw threads disposed on an internal wall thereof. A tubular valve member with a fluid pathway can be disposed within the housing. The valve member can have a tip on its first end. In the region near the tip, one or more fluid holes can be positioned on the valve member so as to provide a fluid pathway there through. The tip can be configured to abut snugly against an internal wall of the male luer in a region at or near the first end of the male luer. In some embodiments, the valve member can also have one or more struts that can be directed towards the first end. The struts can extend axially through a portion of the housing, and the ends of the struts toward the first end can be positioned within a space between the male luer and the shroud on the first end of the housing. A length of medical tubing can be connected to the connector. An end of the tubing can be attached to the second end of the connector by adhesive, welding, threading, or some other means. A resilient member formed from either a metal or an elastomeric material can be positioned with at least a portion within the housing and can bias the valve member toward the closed position.

In the closed state or position, the tip of the valve member can be pressed into close contact with a portion of the internal wall on the first end of the male luer, and fluid flow from the medical tubing through the tubular valve member can be generally impeded. Fluid generally does not exit through the opening on the first end of the male luer because such opening can be blocked by the tip of the valve member.

When a force is applied to move or displace the valve member from the housing, the resilient member can be stressed against its bias and the tip of the valve member can be displaced toward the open position. This displacing force can be applied automatically through the action of connecting the male luer to a female end of another medical implement. As the advancing end of the female connector proceeds up the first end of the housing of the male luer connector, the female connector makes contact with and exerts a force directed towards the second end against the struts of the valve member or against another portion of the valve member, such as the luer tip. This force can move a portion of the valve member towards the second end against the biasing force that can be directed towards the first end exerted by a resilient member. In this opened state, fluid can be permitted to flow through the opposing holes, around the tip of the valve member, and out of the connector through the gap between the tip of the valve member and the internal wall on the first end of the male luer. In some embodiments, the valve member can be automatically advanced in the direction of the second end when the valve member contacts a fluid conduit (e.g., a conduit positioned within a female connector) as the male and female connectors are brought together.

In some embodiments, when the separating force is removed, for example, by releasing the manual grip on the housing and the tubing, or by detaching the female connector from the first end of the housing, the resilient member once again can urge the valve member to the closed position. This can cause the tip on the first end of the valve member to abut closely against a portion of the internal wall in a region near the first end of the male luer, and can impede fluid flow out of the valve.

Also disclosed herein are other features and configurations for the foregoing embodiment, as well as additional embodiments for other connectors with closeable male luers. Such embodiments generally include means for permitting or impeding fluid flow through a male luer on a connector, which can be automatically manipulated upon connection with a corresponding female connector. Such embodiments also include features and configurations that permit the female portion of the male luer connector to be coupled with a corresponding male luer portion of a male luer connector or other component such as a syringe.

Some embodiments disclosed herein relate to a first arrangement of a luer connector having a housing having a hollow bore, a first end, and a second end. A male luer tip can be supported by the housing, the male luer tip configured to rotate with respect to the housing. The male luer tip can have a first open end and a passageway through the male luer tip in fluid communication with the first open end. The luer connector can have a substantially rigid internal member extending into the passageway of the male luer tip toward the first open end of the male luer tip. In some embodiments, at least one of the male luer tip and the internal member can be axially moveable between a first position and a second position relative to the other of the male luer tip and the internal member. The male luer tip and the internal member can be configured to cooperate such that rotation of the male luer tip in a first direction relative to the housing increases an axial displacement between the first open end of the male luer tip and an end portion of the internal member.

In the first position, the end portion of the internal member can provide a substantially fluid-tight seal with respect to the first open end of the male luer tip so as to substantially prevent a flow of fluid through the male luer tip, and in the second position, the end portion of the internal member can be spaced apart from the first open end so that fluid is permitted to flow through the first open end of the male luer tip. In any of the previously described first arrangements, the male luer tip can be configured to rotate with respect to the housing as a female connector is threadedly connected to the luer connector.

In some embodiments, the male luer tip and the internal member can cooperate such that rotation of the male luer tip in a second direction relative to the housing decreases the axial displacement between the first open end of the male luer tip and the end portion of the internal member. In some embodiments, the internal member can be axially moveable relative to the male luer tip, and can have a solid cross-section along at least a substantial portion of the length thereof such that at least a substantial amount of fluid flowing through the luer connector is required to flow around an outside surface of the internal member. Some arrangements of the internal member can have an axial opening through at least a portion of the internal member, the axial opening being in fluid communication with the hollow bore of the housing and being configured to permit fluid to flow through the internal member.

Some embodiments of the luer connector disclosed herein can further have a chamber within the housing, the chamber being configured produce a change in volume as at least one of the male luer tip and the internal member axially moves between the first position and the second position relative to the other of the male luer tip and the internal member. The volume of the chamber can be larger when the male luer tip and the internal member are in the first position. Some arrangements of the internal member can have a helical or angled surface, the helical or angled surface configured to cooperate with the male luer tip and to cause the change in axial displacement between the male luer tip and the internal member as the male luer tip is rotated. The luer connector can have a resilient member configured to bias the male luer tip and the internal member toward the first position.

In some embodiments, an opening in the first open end of the male luer tip and the end portion of the internal member can have an ovular or other non-circular cross-sectional shape. The opening in the first open end of the male luer tip can have a tapered internal wall portion and the end portion of the internal member can have a tapered external wall portion that cooperates with the internal wall portion of the male luer tip. The male luer tip and the internal member can be configured such that relative rotation between the male luer tip and the internal member causes axial displacement between the male luer tip and the internal member.

Some embodiments disclosed herein relate to a luer connector having a housing having a hollow bore, a first end, and a second end, a male luer tip supported by the housing configured to axially move with respect to the housing, the male luer tip having a first open end and a passageway through the male luer tip in fluid communication with the first open end, and a substantially rigid internal member extending into the passageway of the male luer tip toward the first open end of the male luer tip. In some embodiments, the male luer tip can be axially moveable between a first position and a second position relative to the internal member. In the first position, an end portion of the internal member can provide a substantially fluid-tight seal with respect to the first open end of the male luer tip so as to substantially prevent a flow of fluid through the male luer tip, and in the second position, the end portion of the internal member can be spaced apart from the first open end so that fluid is permitted to flow through the first open end of the male luer tip.

In some embodiments of the luer connector, the male luer tip can be configured to axially move from the first position to the second position as a female connector is threadedly connected to the luer connector. Some embodiments of the internal member can have a solid cross-section along at least a substantial portion of the length thereof such that at least a substantial amount of fluid flowing through the luer connector is required to flow around an outside surface of the internal member. In some embodiments, the internal member can have an axial opening through at least a portion of the internal member, the axial opening being in fluid communication with the hollow bore of the housing and being configured to permit fluid to flow through the internal member. The luer connector can further have a resilient member configured to bias the male luer tip toward the first position.

Some embodiments disclosed herein relate to a luer connector having a housing having a hollow bore, a first end, and a second end, a male luer tip supported by the housing configured to rotate with respect to the housing, the male luer tip having an opening in a first end thereof and a passageway through the male luer tip in fluid communication with the opening in the first end thereof. The luer connector can have an internal member extending into the passageway of the male luer tip toward the opening in the first end thereof, the internal member having an opening in a first end thereof and a passageway through the internal member in fluid communication with the opening in the first end thereof. The male luer tip can be configured to be rotatable between a first position and a second position relative to the internal member. In the first position, the opening in the first end of the male luer tip can be substantially offset with respect to the opening in the first end of the internal member so as to substantially prevent a flow of fluid through the male luer tip, and, in the second position, the opening in the first end of the male luer tip can be substantially aligned with respect to the opening in the first end of the internal member so that fluid is permitted to flow through the male luer tip.

In some embodiments, the male luer tip can be configured to rotate in a first direction with respect to the housing from the first position to the second position as a female connector is threadedly connected to the luer connector, and/or to rotate in a second direction with respect to the housing from the second position to the first position as a female connector is threadedly disconnected from the luer connector. In some embodiments, the internal member can be rotationally fixed relative to the housing in some embodiments. The luer tip can be biased toward the first position. The luer connector can be configured such that the male luer tip is prevented from rotating beyond the first or the second position.

BRIEF DESCRIPTION OF THE DRAWINGS

Certain embodiments of this disclosure will now be discussed in detail with reference to the following figures. These figures are provided for illustrative purposes only, and the embodiments are not limited to the subject matter illustrated in the figures.

FIG. 5A is a cross-sectional view of another embodiment of a luer connector in a closed position.

FIG. 5B is an end view of the embodiment of the luer connector shown in FIG. 5A in a closed position.

FIG. 5C is an end view of the embodiment of the luer connector shown in FIG. 5A, showing the embodiment of the luer connector in an open position.

FIG. 5D is a cross-sectional view of the embodiment of the luer connector shown in FIG. 5A taken through line 5D-5D in FIG. 5C.

FIG. 6A is a cross-sectional view of another embodiment of a luer connector in a closed position.

FIG. 6B is a cross-sectional view of the embodiment of the luer connector shown in FIG. 6A in an open position.

FIG. 6C is an end view of the embodiment of the luer connector shown in FIG. 6A in a closed position.

FIG. 6D is an end view of the embodiment of the luer connector shown in FIG. 6B in an open position.

DETAILED DESCRIPTION OF SOME EXEMPLIFYING EMBODIMENTS

In some embodiments, closing mechanisms function to substantially prevent and/or impede fluid from escaping from or entering into the male luer end of a connector, while allowing fluid flow when the male luer is manually opened or engaged with a corresponding female luer. As used herein, terms such as "closed," "sealed," "prevent," or "impede" should be understood as obstructions or barriers to fluid flow. These terms should not be understood to require that a particular structure or configuration achieves a complete fluid closure in all circumstances.

Some medications, including those used during chemotherapy, can be harmful to a patient in certain applications. For example, exposure to the skin can sometimes result in a chemical burn. Inhalation of aerosolized forms of some medications also can be harmful. Thus, control over the containment of the medication is highly desirable.

Figure 1A:
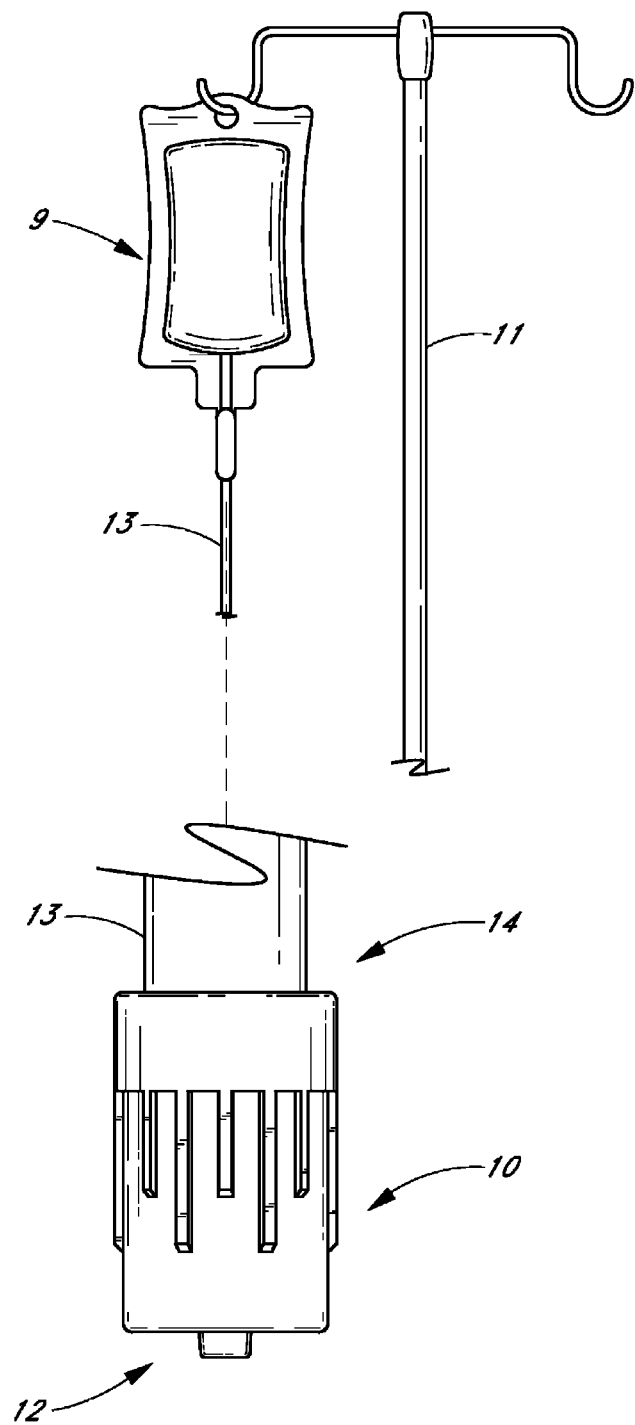
FIG. 1A is a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

FIG. 1A is a perspective view of an embodiment of a male luer connector attached to tubing configured to receive fluid from a hanging gravity-fed IV bag. In some embodiments, the female end of the connector can alternatively be configured to engage a standard male luer end. In FIG. 1A, some embodiments of a closeable male luer connector 10 is shown in a closed position. The luer connector 10 can be attached to a gravity-fed IV bag 9 filled with fluid hanging from a pole stand 11. At the bottom of the bag 9, a section of tubing 13 can be attached. The opposite end of the tubing 13 can be connected to the second end 14 of the luer connector 10. A closing mechanism on the interior of the first end 12 of the luer connector 10 can prevent the fluid contained within the bag 9 from flowing through the tubing 13 and leaking out of the luer connector 10, as long as the luer connector 10 remains in a closed configuration.

The IV delivery system illustrated in FIG. 1A can be easily readied for fluid communication with a patient. In most circumstances, the tubing 13 can be filled with air when it is initially connected to the IV bag 9. If the other end of the tubing 13 can be connected to a closed connector, as illustrated in FIG. 1A, the air cannot escape and fluid cannot enter the tubing 13 from the IV bag 9. In some embodiments, the luer connector 10 can be changed so as to be in the open position until all of the air has been purged through the luer 10 and the fluid in the IV bag 9 fills the tubing 13 and connector 10. This procedure is known as "priming." As soon as the fluid line and connector are properly primed, the health care provider can then change the luer connector 10 to the closed position to stop the flow of fluid through the luer connector 10.

Figure 1B:
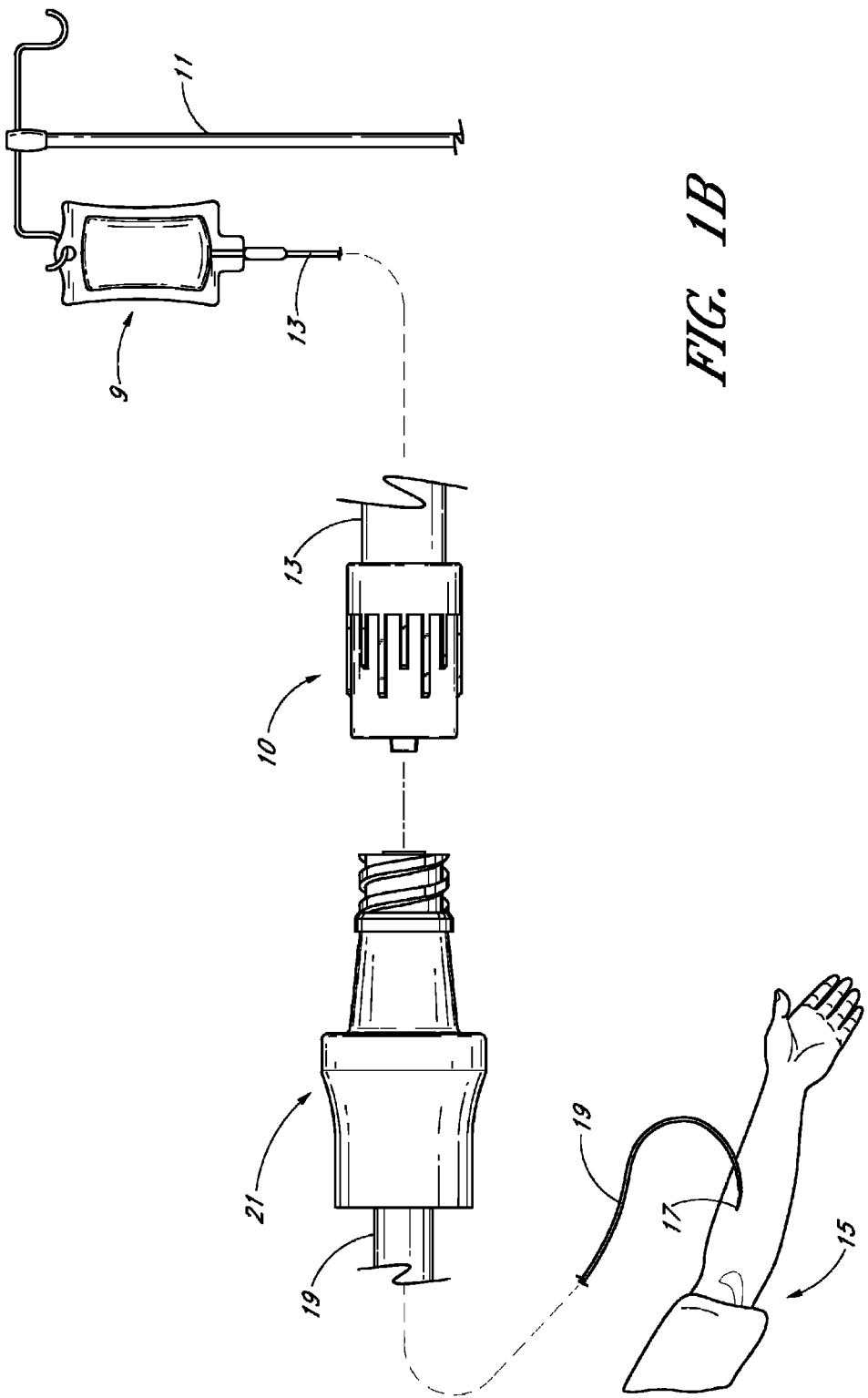
FIG. 1B shows a perspective view of an embodiment of the male luer connector of FIG. 1A being connected to a female connector attached to tubing inserted into a patient.

FIG. 1B shows a perspective view of an embodiment of the male luer connector of FIG. 1A being connected to an exemplifying female connector attached to tubing inserted into a patient. Referring now to FIG. 1B, a catheter 17 has been inserted into a patient's arm 15. The catheter 17 penetrates the skin of the arm 15 and can be fluidly connected with the patient's bloodstream. The catheter 17 can also be connected to a length of medical tubing 19 attached to a female medical connector 21. The example of a female medical connector 21 illustrated in FIG. 1B is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male luer embodiments disclosed herein can be used with other types of female connectors. The tubing 19, catheter 17, and female connector 21 were previously primed with fluid using standard procedures. The luer connector 10 can be primed as described previously and brought into engagement with the female connector 21. As described in further detail below, when the male connector 10 and female connector 21 are engaged, fluid can be permitted to flow from the IV bag 9 into the patient. When the male connector 10 and female connector 21 are disengaged, fluid can be once again prevented from flowing out of the first end 12 of the male connector 10. In general, fluid can also be prevented from flowing out of the opening in the female connector 21.

The embodiment illustrated in FIGS. 1A-1B is described in further detail below. Each of the other embodiments disclosed herein can be used in the illustrated fluid system, and in various modifications and alternatives thereof. Further, it is contemplated that the various embodiments of connectors can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2A:
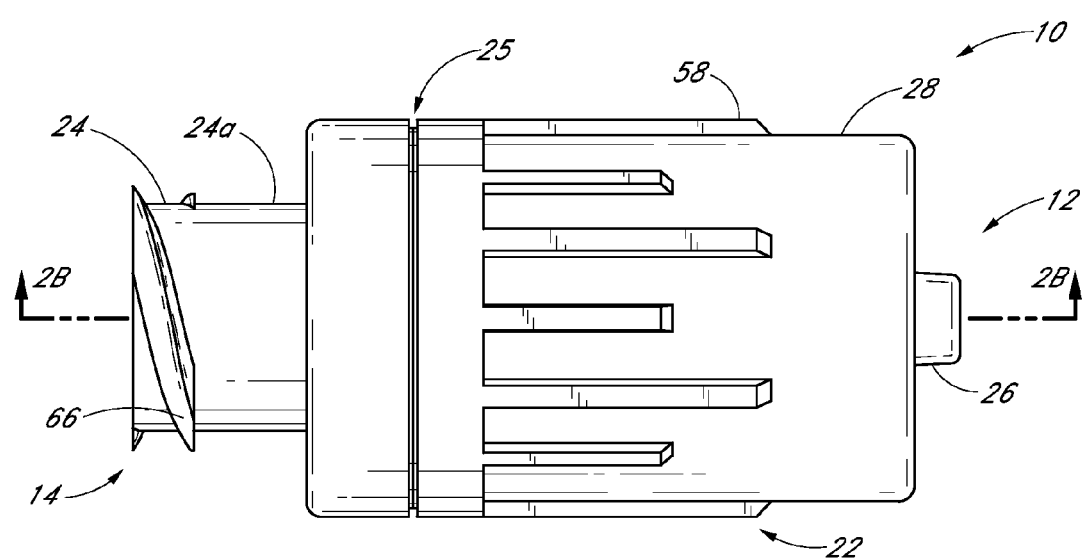
FIG. 2A is a side view of the outside of the embodiment of the luer connector shown in FIG. 1A.
Figure 2B:
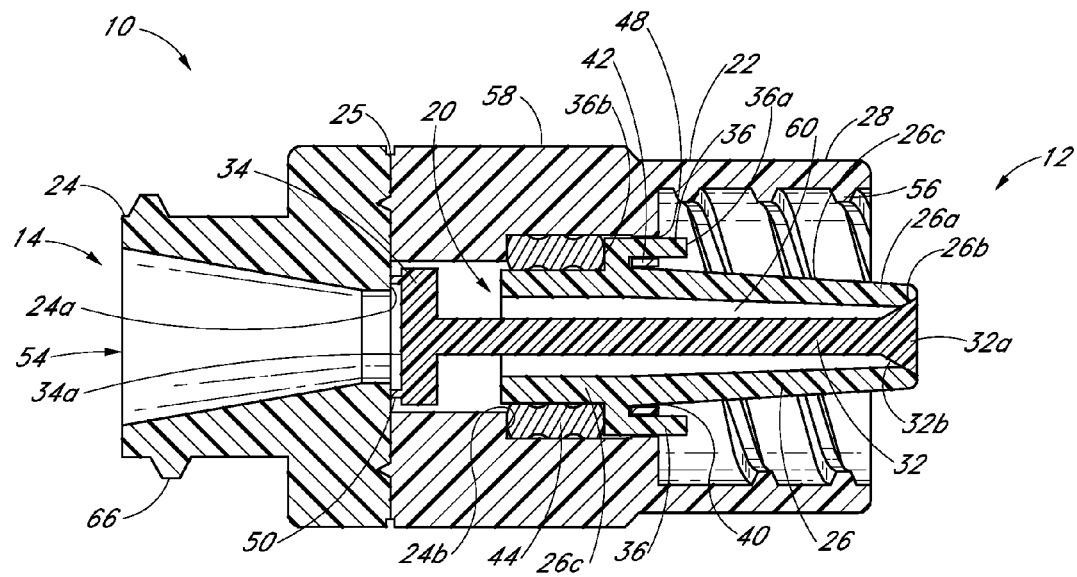
FIG. 2B is a cross-sectional view of the connector taken along the line 2B-2B in FIG. 2A in a closed position.
Figure 2C:
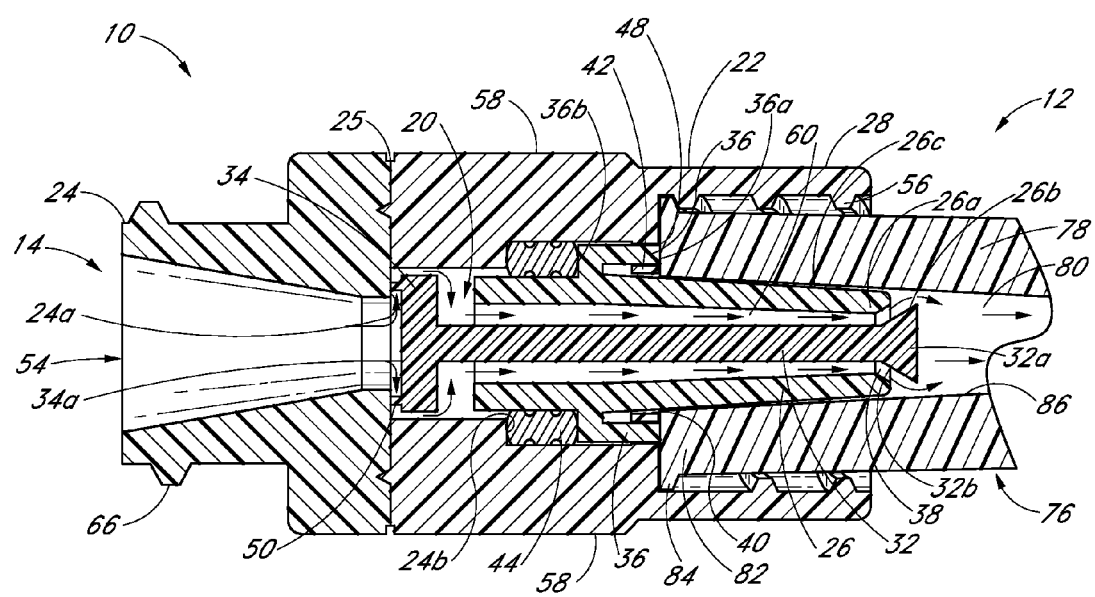
FIG. 2C is a cross-sectional view the connector taken along the line 2B-2B in FIG. 2A in an open position.

Referring now to FIGS. 2A-2C, the embodiment of the closeable male luer 10 of FIGS. 1A-1B is illustrated in greater detail. FIG. 2A is a side view of the outside of the embodiment of the luer connector 10. FIGS. 2B and 2C are cross-sectional views of the luer connector 10 in a closed (or first) position and an open (or second) position, respectively. When the luer connector 10 is in the closed position, fluid can be significantly prevented by the valve member 20 from flowing through the luer connector 10. In the open position, the valve member 20 can be moved to the open position so as to not significantly impede the flow of fluid through the luer connector 10.

As illustrated in FIG. 2A, some embodiments of the assembled luer connector 10 can comprise a housing 22, a port member 24 positioned near the second end 14 of the luer connector 10, a male luer or luer tip 26 positioned near the first end 12 of the luer connector 10, a shroud 28 surrounding at least a portion of the luer tip 26, and the valve member 20 mentioned above supported by the housing 22. The housing 22 can define a part line 25, where the two or more separately formed portions of the housing can be joined. With reference to illustrated embodiment, the port member 24 can be joined with the housing 22 at the part line 25 using ultrasonic welding, epoxy, or other adhesive, interference fits, mechanical connections, unitary constructions, and/or any other suitable coupling method or methods.

In some embodiments, the port member 24 and the housing 22 can be integrally formed, which may require the valve member 20 and the housing 22 to be configured differently to accommodate assembly of these and other components. For example, in some embodiments, where the port member 24 and housing 22 are integrally formed, the luer tip 26, valve tube 32, and sealing member 44 can be assembled within the housing 22 through the shroud 28 at the first end 12 of the luer connector. A retaining member (not illustrated) that can be configured to retain the luer tip 26 and sealing member 44 in the desired position within the housing 22 can be assembled with the housing 22 after the other components have been assembled in the housing 22. In some embodiments, the retaining member (not illustrated) can be a planar disk having openings formed therein and configured to allow the luer tip 26 and struts 36 to translate axially relative to the retaining member. The retaining member could be joined with the housing 22 using ultrasonic welding, epoxy, or other adhesive, interference fits, mechanical connections, and/or any other suitable coupling method or methods.

Additionally, the valve base 34 can be configured so that it is held in a fixed axial position adjacent to the port member 24 after the valve base 34 has been inserted into the housing 22.

In some embodiments, the valve base 34 can be configured so as to form an interference fit with the port member 24 when assembled therewith. In some embodiments, the valve base 34 can be attached to the port member 24 using ultrasonic welds, adhesive, mechanical connections such as tabs, channels, or protrusions, and/or by any other suitable coupling method or methods. Axial openings (not illustrated) can be formed in the valve base 34 or any similar components described herein to allow fluid or medicament to flow therethrough. Thus, in some embodiments, the valve base 34 can be formed to abut flat against one more of the inside surfaces of the port member 24. Alternatively, in some embodiments, the valve base 34 and valve tube 32 can be integrally formed with the port member 24, with the end portion 32a of the valve tube 32 being configured to be attached to the valve tube 32 after the luer tip 26 has been assembled.

Additionally, in the illustrated embodiment, the housing 22 can be configured so that the luer tip 26 projects through an opening 40 formed in an internal wall 42 formed within the housing 22. As will be described in greater detail below, the luer connector 10 can be configured so that the luer tip 22 translates axially relative to the opening 40 formed in the internal wall 42.

In the illustrated embodiment, the valve member 20 can comprise a tube 32 projecting from a valve base 34 toward the first end 12 of the connector 10, and a pair of valve arms or struts 36 also preferably projecting from and supported by the second region 26c of the male luer 26. In the illustrated embodiment, in an assembled configuration, the valve struts 36 can be positioned so as to be adjacent to the tip 26 along the sides of the tip 26. When the luer connector 10 is in the closed position, a portion of the inner surface of the distal portion 32a of the valve tube 32 can be sealingly closed against the inner surface of a portion of the distal portion 26a of the luer tip 26 such that fluid is generally prevented from flowing through the opening 38 formed in the distal end 26a of the luer tip 26.

The following are some sample cross-sectional diameters of the opening 38 preferably formed in the distal end portion 26a of the luer tip 26, or of any opening in any luer tip described herein: approximately 2 mm or less and approximately 0.5 mm to approximately 2.0 mm. Other diameters, either inside or outside the listed ranges can also be used. In some embodiments, the opening 38 can be any desired or otherwise suitable geometry. Regardless of the geometry of the opening 38, the distal portion 32a of the valve tube 32 can be sized appropriately to occupy the space in the opening 38 so that, when the luer connector 10 is in a closed position, a generally fluid tight seal is provided.

In the illustrated embodiment, the luer connector 10 can be configured so that the tube 32 is supported in an axially fixed position relative to the housing 22. In particular, in some embodiments, the aft portion 34a of the valve base 34 can be supported indirectly or directly by the inside surface 24a of the port member 24. In the illustrated embodiment, one or more substantially rigid tabs 50 can be formed so as to project from the aft portion 34a of the valve base 34. The tabs 50 can be configured to abut against the inside surface 24a of the port member 24. The valve base 34 and the tabs 50 are preferably configured to allow fluid or medicament to flow freely around the valve base 34. Further, as mentioned above, the luer tip 26 can be slidably supported so as to translate axially relative to the valve tube 32.

The valve struts 36 that can be supported in a cantilevered disposition by the second end region 26c of the male luer 26 can be configured so as to slide within the openings 48 formed through the internal wall 42 of the housing 22. The number of openings 48 through the internal wall 42 can be equal to the number of the valve struts 36 that are supported by the valve base 34.

An annular sealing member 44 can be positioned between the outside surface of the luer tip 26 and the inside surface of the housing 22 so as to generally prevent any fluid from flowing through either of the openings 40, 48. The sealing member 44 can be formed from a resilient material and configured to provide an axial biasing force on the luer tip 26 toward the first end 12 of the luer connector 10, so as to bias the luer connector 10 to the closed position.

With reference to FIGS. 2B and 2C, the luer connector 10 can be configured so that the sealing member 44 abuts against an aft surface 36b of the valve struts 36 at a first end of the sealing member 44 (e.g., at the end of the sealing member 44 that is closer to the first end 12 of the luer connector 10). Similarly, the luer connector 10 can be configured so that the sealing member 44 abuts against an inside surface 24b of the port member 24 at a second end of the sealing member 44 (e.g., the end of the sealing member 44 that is closer to the second end 14 of the luer connector 10).

In some embodiments, as in the embodiment illustrated in FIGS. 2B-2C, the valve tube 32 or any other valve tube or valve member described with reference to any other embodiments herein can be solid such that a substantial portion of the fluid flowing through the luer connector flows around the outside of the valve member. Moreover, any luer connector embodiment disclosed herein can be configured such that the valve tube is solid or such that the valve tube comprises an opening axially through at least a portion thereof.

In some embodiments, the valve 20, the valve base 34, the valve struts 36, and the protrusion 52 can be integrally formed. In some embodiments, any of the features of the valve member 20, including the valve tube 32, the valve base 34, the valve struts 36, and the protrusion 52, can be separately formed and adhered or otherwise joined together in subsequent manufacturing steps.

In some embodiments, the housing 22 can generally be a tube-like structure with a passageway 54 that can extend away from the second end 14 of the connector 10 through the axial center of the luer connector 10. As such, in some embodiments, when the luer connector 10 is in the open state or position, as illustrated in FIG. 2C, fluid can be permitted to flow from the second end 14 through the port member 24, around the valve base 34 and the tube 32, and out through the opening 38 in the luer tip 26 positioned at the first end 12 of the luer connector 10. With reference to FIGS. 2B and 2C, near the second end 14 of the luer connector 10, the port member 24 and the corresponding section of the fluid passageway 54 can be sized and configured so as to accommodate a section of standard diameter medical tubing inserted therein, or so as to be joinable with any standard or suitably sized medical connector or component, in particular medical implements corresponding to ISO and/or ANSI standards.

In some embodiments, the length of the housing 22 (or any housing described herein) from the second end 14 to the distal end of the luer tip 26 can be approximately 0.75 inch. However, the size of the housing 22 is not so confined. In some embodiments, the length of the housing 22 (or any housing described herein) from the second end 14 to the distal end of the luer tip 26 can be from approximately 0.5 inch to approximately 0.75 inch, or from approximately 0.75 inch to approximately 1.0 inch, or from approximately 1.0 inch to approximately 1.5 inches or more, or from or to any value within these ranges. Thus, the housing 22 can be, but is not necessarily, less than or equal to approximately 1.5 inches from the second end 14 to the distal end of the luer tip 26 so that the weight and bulk of the connector can be minimized. However, the housing 22 can have any length suited for a particular application.

The shroud 28 can have inner threads 56 on an interior wall to securely attach the connector 10 in a removable manner to another medical implement. In other embodiments, the shroud 28 can include other structures or materials for providing a releasable connection, including quick-release mechanisms and other means. As illustrated, the housing 22 and shroud 28 can define a plurality of protrusions 58 or other suitable features on an outer surface to assist the user in firmly grasping and twisting the shroud 28 and the housing 22 with the user's fingers so as to prevent the luer connector 10 from slipping within the user's grasp when the luer connector 10 is twisted. In other embodiments (not illustrated) the housing 22 or shroud 28 may alternatively or additionally define depressions that have upwardly tapering sidewalls that prevent the fingers from sliding off the connector 10, or any other features or materials that prevent the fingers from sliding relative to the connector 10. The protrusions 58 may extend around substantially the entire outer surface of the housing 22 or shroud 28 so that the user's fingers, when positioned on opposite sides of the connector 10, will likely encounter a depression, regardless of the orientation of the connector 10, during use.

With reference to FIGS. 2A-2C, the tip 26 can have a tapered external wall. The diameter of the luer tip 26 can become gradually smaller from the valve base 34 towards the distal end portion 26a of the tip 26. As described above, the tip 26 can define an opening 38 positioned at the distal end portion 26a of the luer tip 26. Near the base of the luer tip 26, which can be the internal wall 42, an interior space 60 (most clearly shown in FIG. 2B) can communicate with the fluid passageway 54 of the luer connector 10 and with the opening 38 so as to provide a fluid flow path through the entire luer connector 10. In some embodiments, the term fluid passageway is meant to refer to the entire fluid pathway through the luer connector. With regard to any of the luer connectors described herein, the dimensions of the housing, shroud, luer tip, or port member (e.g., the male and female ends) or other interfaces can be made to comply with applicable standards and/or regulations, such as the ANSI standards and or ISO standards.

As most clearly illustrated in FIG. 2C, in some embodiments, the distal end portion 32a of the tube 32 can be configured so as to complement the size and shape of the distal end portion 26a of the luer tip 26 so as to define a sealable closing mechanism. In particular, in some embodiments, in the closed position, the inside surface 26b of the luer tip 26 can be positioned against the outside surface 32b of the valve tube 32 so as to provide a generally fluid-tight seal that prevents fluid or other medicament from pass through the opening 38 that can be formed in the distal end 26a of the luer tip 26. Thus, in this configuration, the closing mechanism can be adapted to close the fluid passage extending through the closeable male luer 10 from fluid communication with the external environment, preferably whenever the male luer 10 is not engaged with a female connector.

Thus, as the distal end portion 32a of the tube 32 abuts against the inside surface of the luer tip 26, closure can be formed at or near the first end 12 of the male luer 10. Further, the distal end portion 32a of the tube 32 can be made from, or covered by, a different material than is used to form the tube 32. For example, in some embodiments, the distal end portion 32a can be covered with a softer, more malleable or deformable material that may exhibit better sealing properties as compared to the material used to form the tube 32 so as to provide a better seal between the distal end portion 32a of the tube 32 and the luer tip 26.

Any of the luer connectors described herein may be configured to comprise the features of any of the embodiments of the luer connector 10 described above. Further, in some embodiments, the valve member 20 can be constructed without a fluid path and function as a blocking plunger for fluid flowing around the valve member 20 rather than a means for conveying fluid between the first and second ends of the luer connector 10.

The housing 22 of the illustrated embodiment, or the housing of any embodiment described herein, the port member 24, and any other components disclosed herein can be constructed from any of a number of different materials or combination of materials. In some embodiments, the housing 22 or any housing described herein can be constructed from a relatively rigid material, such as polycarbonate or other polymeric material. The housing 22, port member 24, and/or the valve member of any embodiment described herein, or any of the components of this or any other embodiment, can also be constructed of a hydrophobic material, such as Bayer Makrolon, or any other suitable material.

The length of the valve member 20 can be shorter than the length of the housing 22, but the length of the valve member 20 is not so limited. Any of the valve assemblies described herein, including but not limited to the valve member 20, can be manufactured through injection molding. Finally, although the valve member 20 of the illustrated embodiment is configured as shown in FIGS. 2B-2C, many other configurations are possible.

In some embodiments, as in the embodiments illustrated in FIGS. 2A-2C, one or more protrusions or raised tabs 66 (such as, but not limited to, threads) can be formed on an exterior surface 24a of the port member 24 to facilitate removably attaching a medical implement (not shown) with the second end 14 of the valve member 20. Accordingly, in some embodiments, the exterior surface 24a can be cylindrical except for the protrusions, raised tabs, or other features formed thereon. In some embodiments, the interior surface of the port member 24 can be conically shaped, such that the diameter of the interior surface can be greatest at the portion of the interior surface adjacent to the second end 14 of the luer connector 10. The internal taper of the interior surface can compliment and closely fit with the taper of a typical male luer. Such an internal taper can conform to ANSI and/or ISO standards and/or regulations, such as the standard for medical syringes.

Similarly, the outside surface 26c of the luer tip 26 can be straight or tapered so as to conform to ANSI and/or ISO standards and/or regulations, such as the standard for medical syringes. In some embodiments, the inside surface of the luer tip 26 and the outside surface of the tube 32 can either be straight or can also be tapered. Tapering the inside surface of the luer tip 26 and the outside surface of the tube 32 can help minimize the amount of fluid that flows into and is trapped in the interior space 60 between the tube 32 in the luer tip 26, since, as the tube 32 moves toward a closed position, the distance between the tapered inside surface of the luer tip 26 and the outside surface of the tube 32 would be reduced.

As shown in FIGS. 2A-2C, the closeable luer connector 10 can have a female mating end at the second end 14 of the luer connector 10 and a male luer mating end at the first end 12 of the luer connector 10. The closeable female connector 21 of FIG. 1B (referenced above), as well as other standard female connectors with similar external structure, can also have both female and male ends. In many embodiments, such female connectors can utilize seals or other fluid barriers to impede the flow of fluid on the female end but do not typically do so on the male end. In many of the embodiments of the closeable male luer connectors illustrated and described herein, there may be no seal or other fluid barrier shown on the female end. However, the female end of any of the closeable male luer connectors disclosed herein can be configured to include a closeable female end. For example, the structure for selective fluid-impedance with the female connector 21, or any of the other standard female connectors, could be included within the female end of any of the closeable male luer connectors disclosed herein to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866 entitled Medical Valve and Method of Use filed on Nov. 4, 1994 which disclosure is hereby incorporated by reference as if fully set forth herein. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

With reference again to FIGS. 2B and 2C, the sealing member 44 will now be described in greater detail. In some embodiments, the sealing member 44 can define a generally cylindrical cross-section, as illustrated in FIGS. 2B and 2C. In some embodiments, the sealing member 44 can define a generally circular cross-section. In some embodiments, the sealing member can be substantially cylindrical and can have a bore extending axially through the center thereof. In some embodiments, the sealing member can further comprise a pair of generally rectangular protrusions extending from the sidewalls of the cylindrical portion at diametrically opposed positions. In other embodiments, the protrusions can have different shapes and/or positions, and can assist with positioning and/or aligning the sealing member in the desired position. In some embodiments, the sealing member 44 can also have a generally smaller-diameter middle portion surrounded by two rings at either end with larger diameters. The sealing member can be constructed from a number of different materials. In some embodiments, the sealing member can be made from a silicon-based deformable material. Silicon-based deformable materials are among those that can form fluid-tight closures with plastics and other rigid polymeric materials.

As mentioned, FIG. 2C is a cross-sectional view of the luer connector 10 in an open position, so that fluid can be generally permitted to flow through the luer connector 10. The flow of fluid or medicament through the luer connector 10 is represented by arrows in FIG. 2C. With reference to FIG. 2C, the housing 22, the valve member 20, and the sealing member 44 are in an assembled configuration. As illustrated, the valve member 20 has preferably been moved to the open position by the insertion of the female connector 76. Thus, FIG. 2C illustrates a cross-section and embodiment of the luer connector 10 wherein the valve member 20 has preferably been caused to be opened by the insertion of an exemplifying female connector 76.

With reference to the embodiment illustrated in FIG. 2C, the structure of an exemplifying female connector 76 will now be discussed in further detail. The female connector 76 can comprise an elongate body 78 having a fluid passageway 80 therethrough, and the female connector 76 can have a tip 82 near its proximal end. In some embodiments, the tip 82 of the female connector 76 can have a radially extending surface 84 disposed on its external surface. The female connector 76 can have a fluid conduit (not shown) within the female connector 76. The fluid conduit is not included or required in all female connectors compatible with the connectors 10 disclosed herein. Along a proximal inner surface 86 of the female connector 76, the fluid passageway 80 can be tapered such that the diameter of the fluid passageway 80 decreases in the distal direction.

As shown in FIG. 2B and discussed above, the struts 36 of the valve member 20 can extend through openings 48 in the internal wall 42 of the housing 22 such that, in the closed position, the ends of the struts 36 extend past the internal wall 42 toward the first end 12 of the connector 10. The struts 36 can be configured to engage the proximal end 84 of the female connector 76 as the female connector 76 advances into engagement with the closeable male luer 10. To engage the male luer 10 and female connector 76, as is shown in FIG. 2C, the radially extending surface or surfaces 84 of the female connector 76 can be threaded into the inner threads 56 of the male luer 10. As shown in FIG. 2C, the two luers 10, 76 can be threadedly engaged with one another until the taper of the inner surface 86 of the female luer connector 76 lies adjacent the correspondingly tapered external surface 26c of the tip 26.

As the male luer connector 10 and female connector 76 move towards each other into threaded engagement, the proximal end 84 of the tip of the female connector 76 can contact the struts 36 of the valve member 20. As the male luer connector 10 and female connector 76 move further into threaded engagement, the struts 36, and thereby the luer tip 26, can be moved toward the second end 14 of the male connector 10 by the female connector 76. Thus, as the male luer connector 10 and female connector 76 move further into threaded engagement, the distal end portion 26a of the luer tip 26 can move away from the interior distal end portion 32a of the valve tube 32 in the direction of the second end 14 of the male connector 10. As the luer tip 26 and the valve tube 32 move apart from one another, a space or gap can form between the luer tip 26 and the valve tube 32, permitting fluid to pass through the opening 38 into the fluid passageway 80 of the female connector 76, or vice versa.

In some embodiments, as mentioned above, as the valve struts 36 and luer tip 26 retract into the housing 22, the seal 44 can compress, causing the seal 44 to exert a biasing force on the luer tip 26 toward the closed position or causing the seal 44 to increase the biasing force that this seal 44 exerts on the luer tip 26. The biasing force from the seal 44 can be resisted by the radially extending surface 84 of the female connector 76 contacting the inner threads 56 of the housing 22. However, when the female connector 76 is withdrawn from the male luer 10, the seal 44 can return the sealing portion of the luer tip 26 to the closed position around the valve tube 32.

Despite the relative movement between the housing 22 and the luer tip 26, the sealing member 44 can be configured to maintain a fluid barrier between the outer surface of the tube 32 and the inner surface of the luer tip 26. In some embodiments, where the sealing member 44 comprises the generally rectangular protrusions the position of the sealing member 44 can be maintained by the protrusions. In some embodiments, the sealing member 44 can be positioned by adhering the outer surface of the protrusions to an inner surface of the luer tip 26. In some embodiments, the sealing member 44 can be positioned by adhering the outer surface of the seal 44 to an inner surface of the luer tip 26 or to an outer surface of the valve tube 32. Other suitable means of fixing the position of the sealing member 44 can also be used.

As shown in FIG. 2C, in the opened configuration, the fluid passageway 80 of the female connector 76 can communicate with the passageway 54 of the valve member 20 so as to allow fluid to flow through the passageway 54 and the fluid passageway 80 of the female connector 76 in either direction. Fluid can thereby flow from tubing (not shown) or another connector or conduit that can be attached to second end 14 of the luer connector 10, into the passageway 54 of the housing 22, around the valve base 34, through the interior space 60 within the luer tip 26, and through the opening 38 at the distal end portion 26a of the luer tip 26 and into the fluid passageway 80 of the female connector 76, and vice versa. In some embodiments, the substantially fluid-tight closure can also be formed between corresponding tapers of the outside surface of the tip 26 and the inner surface 86 of the female connector 76.

Figure 3A:
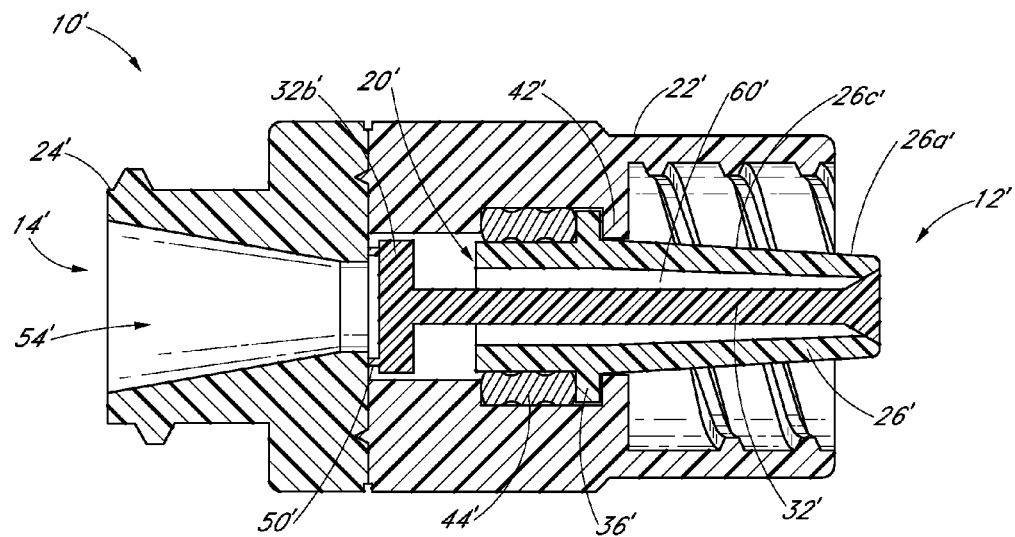
FIG. 3A is a cross-sectional view of another embodiment of a luer connector in a closed position.
Figure 3B:
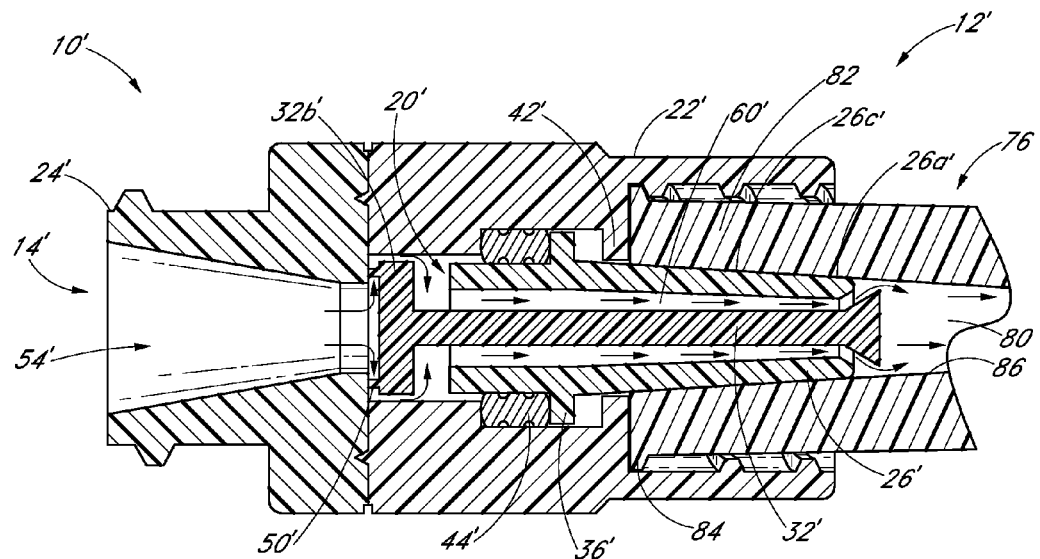
FIG. 3B is a cross-sectional view of the connector in FIG. 3A in an open position.

Referring now to FIGS. 3A-3B, some embodiments of the closeable luer connector 10' will be described in greater detail. In some embodiments, the luer connector 10' can comprise any of the components, features, materials, sizes, geometries, details, or configurations of any of the other luer connectors disclosed herein. FIG. 3A is a cross-sectional view of the luer connector 10' in a first or closed position. As described above, when the valve member 20' of the luer connector 10' is in the closed position, fluid is generally prevented from flowing through the luer connector 10'. FIG. 3B is a cross-sectional view of the embodiment of the luer connector 10' in a second or open position due to the engagement of a female connector 76 with the luer connector. The flow of fluid or medicament through the luer connector 10' is represented by arrows in FIG. 3B. As described above, when the valve member 20' of the luer connector 10' is in the open position, fluid can be generally permitted to flow through the luer connector 10'. As with any embodiment of the luer connector described herein, a perfect seal by the valve member is not required, although such a seal may be preferred in some embodiments.

In some embodiments, the luer connector 10' can be the same or similar to the luer connector 10 described above, except for or in addition to the features and components illustrated and/or described below. First, in some embodiments, as in the illustrated embodiment, the luer tip 36' can be moved from the first, closed position (as illustrated in FIG. 3A) to the second, open position (as illustrated in FIG. 3B) without the use of the actuators or struts 36 as described above with respect to luer connector 10. With reference to FIG. 3B, the luer connector 10' can be threadedly engaged with the closeable female connector 76. The closeable female connector tip 82 of the female connector 76 can have a radially extending surface 84 disposed on its external surface that can engage with the inner threads formed on the inside surface of the shroud 28' of the luer connector 10' to engage the connectors 10', 76 as illustrated.

In some embodiments, as in the illustrated embodiment, the outside surface 26c' of the luer tip 26 can be tapered so that the distal end portion 26a' of the luer tip defines a smaller cross-sectional size or diameter than the portion of the luer tip 26' adjacent to the inner wall 42' of the housing 22'. Additionally, the inside surface 86 of the female connector 76 can be tapered, as illustrated, or can be cylindrical in shape, defining a uniform cross-sectional size or diameter. The female connector 76 can be engaged with the luer connector 10' by any suitable method, including, but not limited to, being threadingly engaged with the luer connector 10' as described above. The luer tip 26' can be configured such that, as the female connector 76 is engaged with the luer connector 10', at least a portion of the inside surface 86 of the female connector 76 will merge with and abut against a portion of the outside surface 26c' of the luer tip 26. At the point when a portion of the inside surface 86 of the female connector 76 has abutted against a portion of the outside surface 26c' of the luer tip 26, further engagement of the female connector 76 relative to the luer connector 10' can cause the luer tip 26' to retract axially toward the second end 14' of the luer connector 10', e.g., toward the open position (also referred to as the second position) as shown in FIG. 3B. In some embodiments, the luer tip 26' can be caused to rotate about the axial centerline of the luer connector 10' as the female connector 76 is increasingly threadingly engaged with the luer connector 10'. Conversely, as the female connector 76 is disengaged from the luer connector 10', the axial biasing force of the seal member 44' will preferably cause the luer tip 26' to return to the closed position (also referred to as the first position) relative to the valve tube 32'.

Figure 4A:
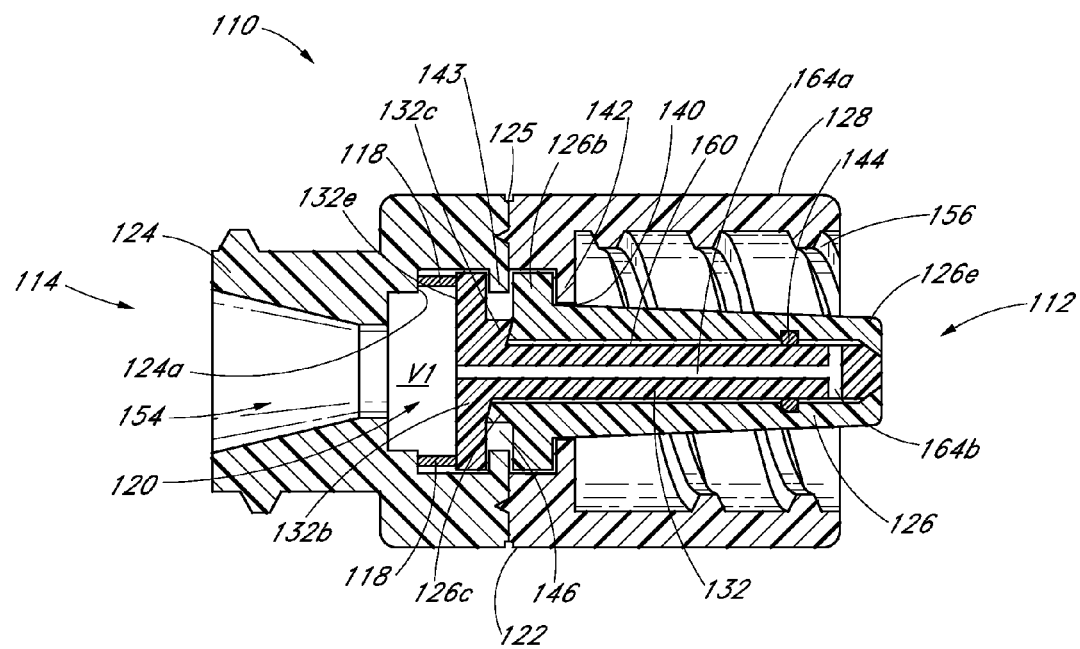
FIG. 4A is a cross-sectional view of another embodiment of a luer connector in a closed position.
Figure 4B:
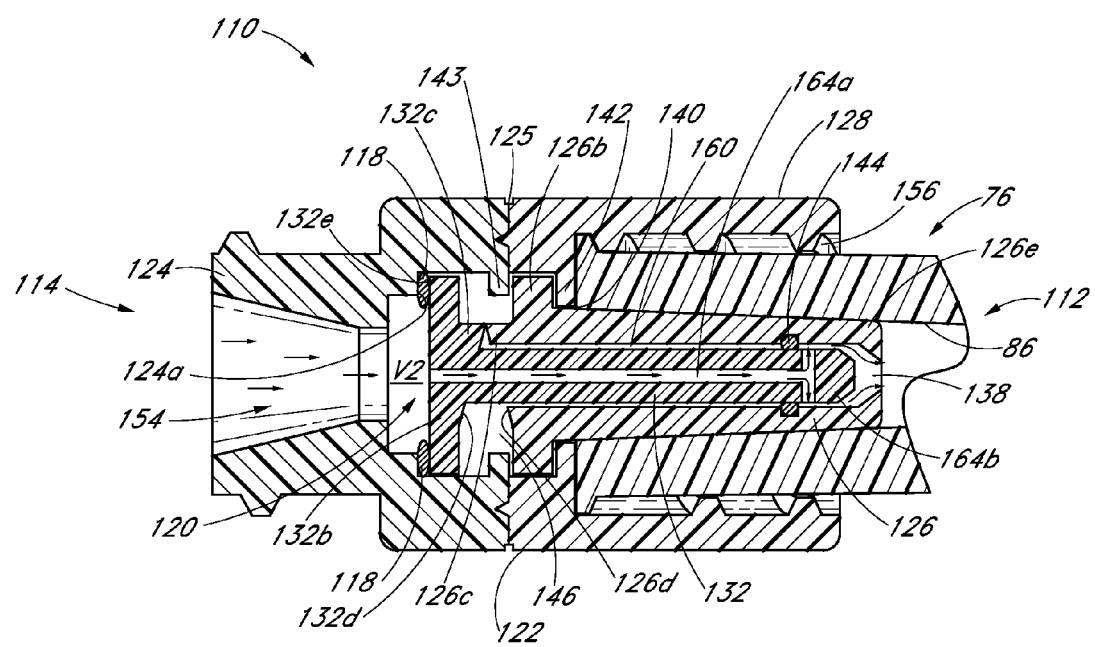
FIG. 4B is a cross-sectional view of the connector in FIG. 4A in an open position.

Referring now to FIGS. 4A-4F, some embodiments of the closeable luer connector 110 will be described. In some embodiments, the luer connector 110 can have any of the components, features, materials, sizes, geometries, details, or configurations of any of the other luer connectors disclosed herein. FIG. 4A is a cross-sectional view of the luer connector 110 in a closed position. As described above, when the valve member 120 of the luer connector 110 is in the closed position, fluid is generally prevented from flowing through the luer connector 110. FIG. 4B is a cross-sectional view of the embodiment of the luer connector 110 in an open position due to the engagement of a female connector 76 with the luer connector. The flow of fluid or medicament through the luer connector 110 is represented by arrows in FIG. 4B. As described above, when the valve tube 132 (also referred to as an internal member) of the luer connector 110 is in the open position, fluid can be generally permitted to flow through the luer connector 110. When the valve tube 132 is in a closed position, fluid can be generally prevented from flowing through the luer connector 110. As with any embodiment of the luer connector described herein, a perfect seal by the valve member is not required, although such a seal may be preferred in some embodiments.

As illustrated in FIG. 4A, some embodiments of the assembled luer connector 110 can comprise a housing 122, a port member 124 positioned near the second end 114 of the luer connector 110, a luer tip 126 positioned near the first end 112 of the luer connector 110, a shroud 128 surrounding at least a portion of the luer tip 126, a seal 118, and a valve member 120. As illustrated, the seal 118 and the valve member 120 can be supported within the housing 122. In the illustrated embodiment, the valve member 120 can comprise a luer tip 126 and a valve tube 132. In some embodiments, the valve tube 132 can be positioned at least partially within the opening 138 that can be formed in the luer tip 126.

In some embodiments, as in the illustrated embodiment, the housing 122 can define an opening 140 through which the luer tip 126 can project. With reference to FIG. 4A, the luer connector 110 can be configured so that the luer tip 126 projects toward the first end 112 of the luer connector 110. The luer tip 126 is preferably co-axially aligned with the centerline of the housing 122, port member 124, and the shroud 128. The opening 140 can be sized and configured so as to provide radial support to the luer tip 126 so that the luer tip 126 remains generally co-axially aligned with the centerline of the housing 122. The luer connector 110 also can be configured so that the luer tip 126 is axially supported within the housing 122. Additionally, for reasons that will be described in greater detail below, the housing 122 and opening 140 can be sized and configured so that the luer tip 126 can freely rotate at least within a predetermined angular range relative to the housing 122 and shroud 128.

Figures 4C, 4D:
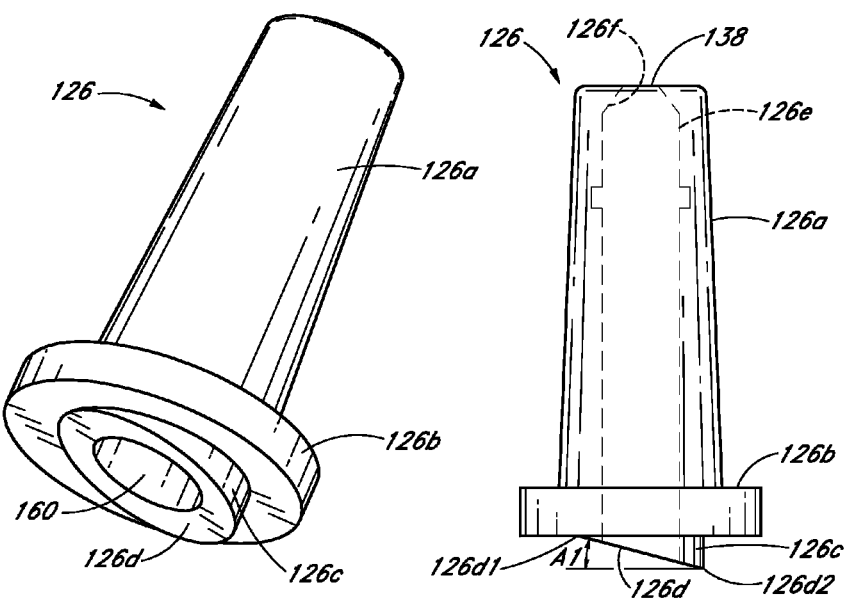
FIG. 4C is a perspective view of an embodiment of a luer tip of the embodiment of the luer connector shown in FIG. 4A.
FIG. 4D is a side view of the embodiment of the luer tip shown in FIG. 4C.

FIGS. 4C and 4D are a perspective view and a side view, respectively, of an embodiment the luer tip 126 of the embodiment of the luer connector 110. As most clearly illustrated in FIGS. 4C-4D, in some embodiments, the luer tip 126 can be formed so as to define a generally conical, tapered outside surface 126a projecting from a planar base portion 126b toward the first end 112 of the luer connector 110. Additionally, in some embodiments, the luer tip 126 can be formed so as to define a helical or angled portion 126c projecting from the base portion 126b toward the second end 114 of the luer connector 110. The angled portion 126c can define a generally planar angled surface 126d. As will be discussed below, the angled portion 126c can project from the base portion 126b to any length suitable to cause the valve tube 132 to move axially away from the luer tip 126 when the luer tip 126 is rotated relative to the valve tube 132, causing the luer connector 110 to change from the closed to the open position when the luer tip 126 is rotated relative to the valve tube 132.

The luer tip 126 can also be configured to define a generally cylindrical opening 160 through at least a portion of the luer tip 126, with the opening 160 being generally axially aligned with the axial centerline of the luer tip 126. The end portion 126e of the luer tip 126 preferably defines an angled or tapered surface 126f, wherein the inside surface of the luer tip 126 can be generally conical in shape so that the size of the opening 138 at the distal tip of the luer tip 126 is reduced relative to the portion of the opening 160 adjacent the opening 138.

Figures 4E, 4F:
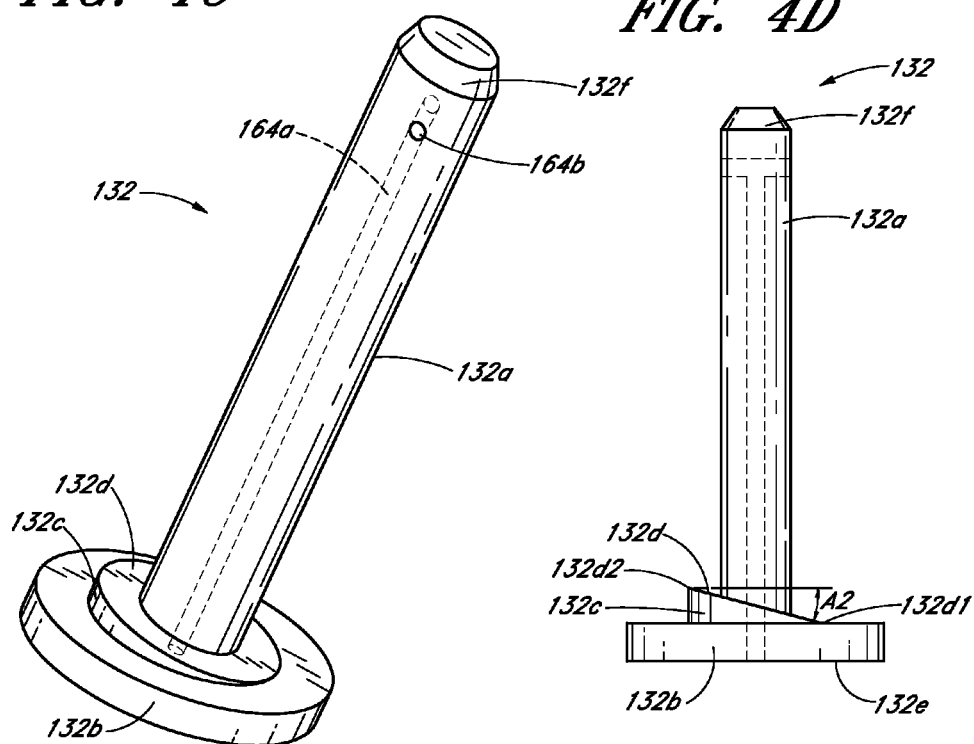
FIG. 4E is a perspective view of an embodiment of a valve tube of the embodiment of the luer connector shown in FIG. 4A.
FIG. 4F is a side view of the embodiment the valve tube shown in FIG. 4E.

FIGS. 4E and 4F are a perspective view and side view, respectively, of an embodiment a valve tube 132 of the embodiment of the luer connector 110. As most clearly illustrated in FIGS. 4E-4F, in some embodiments, the valve tube 132 can be formed so as to define a generally cylindrical outside surface 132a that is sized and configured to be received within a generally cylindrically shaped opening 160 that can be formed in the luer tip 126.

As illustrated in FIGS. 4E and 4F, the outside surface 132a of the valve tube 132 can project from the base portion 132b of the valve tube 132 toward the first end 112 of the luer connector 110. Additionally, the valve tube 132 can define a helical or angled portion 132c that projects toward the first end 112 of the luer connector 110 from the base portion 132b of the valve tube 132. The angled portion 132c can surround the outside surface 132a of the valve tube 132. The angled portion 132c can define a generally planar surface 132d that, in some embodiments, can be sized, angled, and configured to complement the angled portion 126c of the luer tip 126.

Alternatively, in some embodiments, either the luer tip 126 or the valve tube 132 can be formed so that either component defines a tab, pin, or other projection (not illustrated) instead of the angled portion 126c, 132c that substantially performs the same function as either angled portion. For example, in some embodiments, a tab, pin, or other projection (not illustrated) can project from the base portion 126b of the luer tip 126 toward the second end 114 of the luer connector 110 (instead of the angled portion 12bc) that can interact with the angled surface 132c of the valve tube 132 so as to cause the valve tube 132 to move away from the luer tip 126 and, hence, cause the opening 138 in the luer tip 126 to open as the luer tip 126 is rotated relative to the valve tube 132.

In some embodiments, the luer tip 126 can be axially and radially supported by the housing 122 in a manner that permits the luer tip 126 to rotate substantially freely relative to the housing 122, preferably within a defined angular range, but in a manner that substantially prevents axial movement of the luer tip 126 relative to the housing 122 and with enough rotational resistance to inhibit accidental opening of the connector 110. For example, detents can be formed on the luer connector 110 to inhibit accidental rotation of the male luer tip 126 relative to the housing 122. In some embodiments, the luer tip 126 can be configured to move axially relative to the housing 122. With reference to FIGS. 4A and 4B, the luer tip 126 can be axially supported by an internal wall 142 that can be formed on the inside of the housing 122 so as to prevent the luer tip 126 from translating axially toward the first end 112 of the luer connector 110 relative to the housing 122. Similarly, the luer tip 126 can be axially supported by an internal wall 143 that can be formed on the inside of the port member 124 so as to prevent the luer tip 126 from translating axially toward the second end 114 of the luer connector 110 relative to the housing 122. Additionally, in some embodiments, the port member 124 can be adhered, fused, welded, or otherwise attached to the housing 122 along the part line surface 125 after the luer tip 126 has been assembled within the housing 122.

The valve tube 132 can be supported within the housing 122 as shown in FIGS. 4A-4B. As illustrated therein, the valve tube 132 can be axially supported by an internal wall 143 that can be formed in the housing 122 so as to prevent the valve tube 132 from translating axially toward the first end 112 of the luer connector 110 relative to the housing 122. Additionally, the luer connector 110 can be configured so as to prevent the valve tube 132 from rotating relative to the housing 122 or port member 124. In particular, in some embodiments, the port member 124 and the base portion 132b of the valve tube 132 can define splines, channels, protrusions, tabs, pins, or other indexing features configured to prevent the valve tube 132 from rotating relative to the housing 122 or port member 124. As will be discussed in greater detail below, in some embodiments, the valve tube 132 is preferably prevented from rotating relative to the port member 124 or housing 122 so that the luer tip 126 can rotate relative to the valve tube 132 and cause the valve tube 132 to open and close in response to the rotation of the luer tip 126.

Additionally, with reference to FIGS. 4A and 4B, a seal 118 can be attached to the inside surface 124a of the port member 124 and to the base portion 132b of the valve tube 132. In some embodiments, the seal 118 can define an annular or cylindrical shape so that generally all of the fluid or medicament flowing through the port member 124 is caused to flow through the axial opening 164a in the valve tube 132 (e.g., so as to generally prevent fluid or medicament from flowing around the base portion 132b of the valve tube 132) and at least one opening 164b in communication with the axial opening 164a. The opening 164b can be positioned approximately transverse to the axial opening 164a and/or the valve tube 132. Additionally, in some embodiments, the seal 118 can be formed from a resilient material that exerts a biasing force on the valve tube 132 that biases the valve tube 132 toward the first end 112 of the luer connector 110 (e.g., biases the valve tube 132 toward the closed position relative to the luer tip 126).

With reference to FIG. 4D, the angled portion 126c of the luer tip 126 can define a planar surface 126d. In some embodiments, the surface 126d or surface 132d can be curved, or define other suitable shapes. As illustrated in FIG. 4D, the planar surface 126d can define an angle A1 relative to a horizontal reference plane. Similarly, with reference to FIG. 4F, the angled portion 132c of the valve tube 132 can define a planar surface 132d. As illustrated in FIG. 4F, the planar surface 132d can define an angle A2 relative to a horizontal reference plane. In some embodiments, the value of angle A1 can be approximately equal to the value of angle A2. In some embodiments, the value of the angle A1 can be different than the value of angle A2.

In some embodiments, the value of the angle A1 and/or A2 can be approximately 30 degrees. In some embodiments, the value of the angle A1 and/or A2 can be from approximately 15 degrees to approximately 75 degrees. In some embodiments, the value of angle A1 can be different as compared to the value of angle A2.

As will now be described in greater detail below, in the assembled configuration, as illustrated in FIGS. 4A and 4B, rotation of the luer tip 126 relative to the valve tube 132 can cause the valve member 120 of the luer connector 110 to move between the open position and the closed position. As mentioned above, in some embodiments, the seal 118 can exert a biasing force on the valve tube 132 that can cause the valve tube 132 to move into or remain in contact with the luer tip 126. In particular, the seal 118 can cause the planar surface 132d of the valve tube 132 to abut against the planar surface 126d, as is illustrated in FIGS. 4A and 4B. With reference to FIGS. 4A, 4D, and 4F, when the highest point 126d2 on the planar surface 126d (e.g., the point on the surface 126d that is furthest away from the base portion 126b) is approximately radially aligned with the lowest point 132d1 on the planar surface 132d (e.g., the point on the surface 132d that is closest to the base portion 132b) as is illustrated in FIG. 4A, the aft portion 132f of the valve tube 132 can generally be in sealing contact with the inside surface of the aft portion of the luer tip 126, so as to generally sealingly close the opening 138. Conversely, when the highest point 126d2 on the planar surface 126d is approximately radially aligned with the highest point 132d2 on the planar surface 132d (e.g., the point on the surface 132d that is furthest away from the base portion 132b) as is illustrated in FIG. 4B, the aft portion 132f of the valve tube 132 will preferably be spaced apart from the inside surface of the aft portion of the luer tip 126, so that the opening 138 is unsealed by the valve tube 132.

Accordingly, the relative rotation of the luer tip 126 with respect to the valve tube 132 can cause the valve tube 132 to move between the opened and closed position. In some embodiments, the luer tip 126 can be configured so as to define rotational limits or stops arranged to ensure that, as a female connector 76 is threadedly engaged with the luer connector 110 as described in greater detail below, the luer tip 126 stops rotating at a desired radial position wherein the valve tube 132 has opened a sufficient amount to permit fluid or medicament to flow through the luer connector 110. Similarly, the rotational limits or stops can be arranged to ensure that, as the female connector 76 is threadedly disengaged from the luer connector 110, the luer tip 126 stops rotating at a desired radial position that allows the valve tube 132 to sealingly close against the inside surface of the luer tip 126 by the bias force provided by the resilient seal 118. In particular, in some embodiments, the luer tip 126 and the housing 122 can define splines, channels, protrusions, tabs, pins, or other indexing features configured to control the range of rotation of the luer tip 126 relative to the housing 122. When the luer connector 110 is in the closed position, the outer surface of the distal portion 132a of the valve tube 132 can be sealingly closed against the inner surface of the distal portion of the luer tip 126 such that fluid can be generally prevented from flowing through the opening 138 formed in the distal end portion of the luer tip 126.

As mentioned, in the illustrated embodiment, the tube 132 can be slidably supported so as to translate axially within the luer tip 126. Further, an annular sealing member 144 can be positioned between the outside surface of the valve tube 132 and the inside surface of the luer tip 126 to prevent fluid from flowing into the chamber 146. The sealing member 144 can comprise any of the materials, geometries, sizes, or other details or configurations of any other seal or a sealing member described herein. In some embodiments, the sealing member 144 can be formed from the same material as the valve tube 132 and can be formed integrally with the valve tube 132. In some embodiments, the sealing member 144 can be formed from a different material as compared to the valve tube 132. In some embodiments, the sealing member 144 can be formed separately from the valve tube 132 and positioned at the desired axial location of either the valve tube 132 or the inside surface of the luer tip 126. In some embodiments, the inside surface of the luer tip 126 and/or the outside surface of valve tube 132 can comprise features such as channels or depressions to secure the sealing member 144 in the desired location.

In some embodiments, the seal 118 can be resilient and biased toward an expanded position, as illustrated in FIG. 4A, so as to exert a force on the valve tube 132 that biases the valve tube 132 toward the closed position. In particular, in the illustrated embodiment, the seal 118 can bias the valve tube 132 to sealably close against the inside surface of the luer tip 126. Further, the seal 118 can be configured so that the volume generally contained within the interior portion of the seal 118 when the valve member 120 is in the closed position (which is represented by V1 in FIG. 4A) can be greater than the volume contained within the interior portion of the seal 118 when the valve member 120 is in the open position (which is represented by V2 in FIG. 4B). Thus, the volume of fluid contained within the interior portion of the seal 118 can decrease when the valve member 120 moves from the closed position to the open position and can increase when the valve member 120 moves from the open position to the closed position. By increasing the volume of space within the seal 118 as the valve member 120 moves to the closed position, the seal 118 can create reduced pressure or a force of suction that can reduce the amount of fluid or medicament that can flow through or drip out of the opening 138 as the valve member 120 is in the process of closing by drawing such fluid back into the volume of space within the interior of the seal 118.

In some embodiments, the seal 118, the tube 132, and the sealing member 144 can all be integrally formed from the same material. In some embodiments, however, any of these features can be formed separately and supported in the desired position as described above or in any other suitable manner. The housing 122 can be generally a tube-like structure with a passageway 154 that can extend from the second end 114 of the connector 110 through the axial center of the luer connector 110. As such, in some embodiments, when the luer connector 110 is in the open configuration as illustrated in FIG. 4B, the passageway 154 can permit fluid to flow from the second end 114 through the port member 124, the seal 118, the opening 164a in the tube 132, and out through the opening 138 in the luer tip 126 positioned at the first end 112 of the luer connector 110.

With reference to FIGS. 4A and 4B, near the second end 114 of the luer connector 110, the port member 124 and the corresponding section of the fluid passageway 154 can be sufficiently wide so as to accommodate a section of standard-diameter medical tubing inserted therein. The length, diameter, or other features and of the housing 122 (or any housing described herein) can be the same as any other housing described herein.

Additionally, the shroud 128 can be sized and configured as described above or as desired to securely or removably attach the luer connector 110 to another medical implement. Further, the housing 122, tip 126, seal 118, or any other components or features of the luer connector 110 can have or be made from any of the materials, shapes, features, sizes, or other configurations or details described with regard to any other tip member disclosed herein. As with other embodiments of the luer tip, the luer tip 126 can be made to comply with applicable standards and/or regulations, such as the ANSI and/or ISO standards.

With reference to FIG. 4B, as the male luer connector 110 and female connector 76 move towards each other into threaded engagement, the inside surface 86 of the female connector 76 can contact the outside surface of the luer tip 126. This can cause a fluid tight seal between the inside surface 86 of the female connector 76 and the outside surface of the luer tip 126. As the male luer connector 110 and female connector 76 move further into threaded engagement, the contact force between the inside surface 86 of the female connector 76 and the outside surface of the luer tip 126 can cause the luer tip 126 to rotate substantially in unison with the female connector 76. This can cause in the luer tip 126 to rotate relative to the valve tube 132, causing the distal end portion 132a of the valve tube 132 to move away from the interior distal end portion 126a of the luer tip 126, as described above. As the tube 132 and luer tip 126 move apart from one another, a gap can form between the tube 132 and the luer tip 126, permitting fluid to pass through the opening 138 into the fluid passageway 80 of the female connector 76, or vice versa.

As discussed above, as the valve tube 132 opens and causes the seal 118 to be compressed, the volume of fluid that can be contained within the seal 118 accordingly decreases. In some embodiments, when a constant source of positive pressure is imparted on the passageway 54 at the second end 114 of the luer connector 110, while the seal 118 is being compressed (which decreases the volume of fluid in the seal 118), the fluid within the seal 118 can be subjected to an increased pressure due to the compression of the seal 118. In some embodiments, this increased pressure can cause the fluid within the seal 118 to flow through the passageway 154 toward the first end 112 of the luer connector 110 at an increased rate, until the seal 118 is no longer being compressed.

Conversely, in some embodiments, when the female connector 76 is removed from the luer connector 110, the interaction between the inside surface 86 of the female connector 76 and the outside surface of the luer tip 126 can cause the luer tip 126 to rotate relative to the valve tube 132, causing the valve tube 132 to move to the closed position relative to the luer tip 126. As the valve tube 132 moves toward the closed position, the volume within the seal 118 can increase back to volume V1. The expansion of the interior volume of the seal 118 can cause a reduced pressure or suction to be generated within the seal 118, drawing at least some of the fluid that is within the opening 164a back into the volume of space within the seal 118. In some embodiments, the luer connector 110 may be used to control the flow of fluids or medicaments that are harmful or corrosive, such that preventing even a few drops from dripping out of the opening 138 as the female connector 76 is being removed can be beneficial.

Figures 5E, 5F:
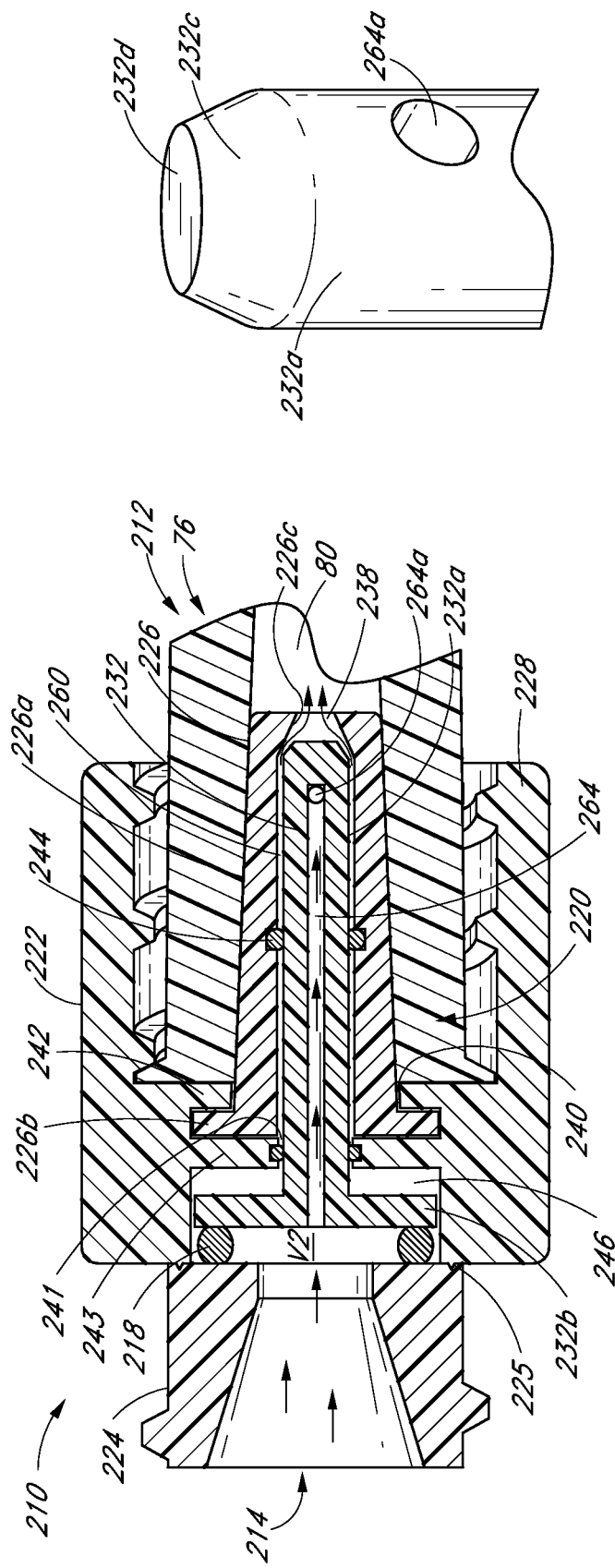
FIG. 5E is a cross-sectional view of the embodiment of the luer connector shown in FIG. 5A taken through line 5E-5E in FIG. 5C.
FIG. 5F is a perspective view of a portion of an embodiment of a valve tube of the embodiment of the luer connector shown in FIG. 5A.

Referring now to FIGS. 5A-5F, another embodiment of a closeable luer connector 210 will be described. FIG. 5A is a cross-sectional view of the luer connector 210, showing the luer connector 210 in a closed position. FIG. 5B is an end view of the luer connector 210, showing the luer connector 210 in a closed position. FIG. 5C is an end view of the luer connector 210, showing the embodiment of the luer connector in an open position. FIG. 5D is a cross-sectional view of the luer connector 210 taken through line 5D-5D in FIG. 5C, showing the luer connector 210 in an open position. FIG. 5E is a cross-sectional view of the luer connector 210 taken through line 5E-5E in FIG. 5C, showing the luer connector 210 in an open position. FIG. 5F is a perspective view of a portion of an embodiment of a valve tube 232 (also referred to as an internal member) of the luer connector 210.

In some embodiments, the luer connector 210 can have or be made from any of the components, features, materials, sizes, geometries, details, or configurations of any of the other luer connectors disclosed herein. As mentioned, FIG. 5A is a cross-sectional view of the luer connector 210 in a closed position so that fluid is generally prevented from flowing through the luer connector 210. FIG. 5D is a cross-sectional view of the embodiment of the luer connector 210 in an open position due to the engagement of a female connector 76 with the luer connector. The flow of fluid or medicament through the luer connector 210 is represented by arrows in FIG. 5D. As described above with reference to other luer connectors, when the valve tube 232 of the luer connector 210 is in the open position, fluid can be generally permitted to flow through the luer connector 210. Similarly, when the valve tube 232 is in a closed position, fluid can be generally prevented from flowing through the luer connector 210. As with any embodiment of the luer connector described herein, a perfect seal by the valve member is not required, although such a seal may be preferred in some embodiments.

In some embodiments, the luer connector 210 can be the same or similar to the luer connector 110 described above, except for or in addition to the features and components illustrated and/or described below. Accordingly, in some respects, the luer connector 210 can operate in the same or similar manner as compared to the luer connector 110 described above. As illustrated in FIG. 5A, some embodiments of the assembled luer connector 210 can comprise a housing 222, a port member 224 positioned near the second end 214 of the luer connector 210, a luer tip 226 positioned near the first end 212 of the luer connector 210, a shroud 228 surrounding at least a portion of the luer tip 226, a seal 218, and a valve member 220. As illustrated, the seal 218 and the valve member 220 can be supported within the housing 222. In the illustrated embodiment, the valve member 220 can comprise a luer tip 226 and a valve tube 232. In some embodiments, the valve tube 232 can be positioned at least partially within the opening 260 that can be formed in the luer tip 226.

In some embodiments, as in the illustrated embodiment, the housing 222 can define an opening 240 through which the luer tip 226 can project. With reference to FIG. 5A, the luer connector 210 can be configured so that the luer tip 226 projects toward the first end 212 of the luer connector 210. The luer tip 226 is preferably co-axially aligned with the centerline of the housing 222, port member 224, and the shroud 228. The opening 240 can be sized and configured so as to provide radial support to the luer tip 226 so that the luer tip 226 remains generally co-axially aligned with the centerline of the housing 222. In some embodiments (not shown), a seal can be positioned between the outside surface of the luer tip 226 and the opening 240. The luer connector 210 also can be configured so that the luer tip 226 is axially supported within the housing 222. Additionally, for reasons that will be described in greater detail below, the housing 222 and opening 240 can be sized and configured so that the luer tip 226 can freely rotate completely around or within a predetermined angular range relative to the housing 222, the shroud 228, and the valve tube 232.

In some embodiments, the luer tip 226 can be formed so as to define a generally conical, tapered outside surface 226a projecting from a planar base portion 226b toward the first end 212 of the luer connector 210. Additionally, in some embodiments, the luer tip 226 can be formed so as to define an angled surface 226c on the inside of the end portion of the luer tip 226. As will be discussed below, the angled surface 226c can be configured to cause the valve tube 232 to move axially away from the luer tip 226 when the luer tip 226 is rotated relative to the valve tube 232, causing the luer connector 210 to change from the closed to the open position when the luer tip 226 is rotated relative to the valve tube 232. The luer tip 226 can also be configured to define a generally cylindrical opening 260 through at least a portion of the luer tip 226, with the opening 260 being generally aligned with the axial centerline of the luer tip 226.

In some embodiments, the valve tube 232 can be formed so as to define a generally cylindrical outside surface 232a that is sized and configured to be received within a generally cylindrically shaped opening 260 that can be formed in the luer tip 226. As illustrated in FIGS. 5A and 5D, the outside surface 232a of the valve tube 232 can project from the base portion 232b of the valve tube 232 toward the first end 212 of the luer connector 210. Further, as illustrated, the end portion of the valve tube 232 can define an angled, ovular, or other non-circular shape such that the distal end surface 232d of the valve tube 232 defines an ovular or other non-circular perimeter. Similarly, in some embodiments, the opening 238 formed in the end of the luer tip 226 can define an ovular, or other non-circular shape.

In some embodiments, the luer tip 226 can be axially and radially supported by the housing 222 in a manner that permits the luer tip 226 to rotate freely relative to the housing 222 preferably within a defined angular range, but in a manner that substantially prevents axial movement of the luer tip 226 relative to the housing 222. In some embodiments, the luer tip 226 can be configured to move axially relative to the housing 222. With reference to FIGS. 5A and 5D, the luer tip 226 can be axially supported by an internal wall 242 that can be formed on the inside of the housing 222 so as to prevent the luer tip 226 from translating axially toward the first end 212 of the luer connector 210 relative to the housing 222. Similarly, the luer tip 226 can be axially supported by an internal wall 243 that can be formed on the inside of the port member 224 so as to prevent the luer tip 226 from translating axially toward the second end 214 of the luer connector 210 relative to the housing 222. In some embodiments, the port member 224 can be adhered, fused, welded, or otherwise attached to the housing 222 along the part line surface 225 after the luer tip 226 has been assembled within the housing 222. In some embodiments, the housing 222 can define additional or different part lines so that all of the internal components such as the valve tube 232, the seal 218, and the luer tip 226 can be assembled therein.

The valve tube 232 can be supported within the housing 222 as shown in FIGS. 5A, 5B, and 5E. As illustrated therein, the valve tube 232 can be axially supported within an opening 241 that can be formed in the internal wall 243 of the housing 222 to laterally constrain the valve tube 232. As illustrated, a seal can be supported by the internal wall 243 to seal the opening 241. In the illustrated embodiment, the internal wall 243 can prevent the valve tube 232 from translating axially toward the first end 212 of the luer connector 210 relative to the housing 222. Additionally, the luer connector 210 can be configured so as to prevent the valve tube 232 from rotating relative to the housing 222 or port member 224. In particular, in some embodiments, the port member 224 and the base portion 232b of the valve tube 232 can define splines, channels, protrusions, tabs, pins, or other indexing features configured to prevent the valve tube 232 from rotating relative to the housing 222 or port member 224. As will be discussed in greater detail below, in some embodiments, the valve tube 232 can be prevented from rotating relative to the port member 224 or housing 222 so that the luer tip 226 can rotate relative to the valve tube 232 and cause the valve tube 232 to open and close in response to the rotation of the luer tip 226.

Additionally, with reference to FIGS. 5A and 5E, a seal 218 can be attached to the inside surface 224a of the port member 224 and to the base portion 232b of the valve tube 232. In some embodiments, the seal 218 can define an annular or cylindrical shape so that generally all of the fluid or medicament flowing through the port member 224 is caused to flow through the axial opening 264 and the transverse opening 264a in the valve tube 232 (e.g., so as to generally prevent fluid or medicament from flowing around the base portion 232b of the valve tube 232). Additionally, in some embodiments, the seal 218 can be formed from a resilient material that exerts a biasing force on the valve tube 232 that biases the valve tube 232 toward the first end 212 of the luer connector 210 (e.g., biases the valve tube 232 toward the closed position relative to the luer tip 226). In some embodiments, seal 218 can be a spring or other biasing device that biases the valve tube 232 towards the first end 212 of the luer connector 210, but does not contain fluid flowing through the connector 210. Rather, fluid would be prevented from flowing around the valve tube 232 toward the first end 212 by seal 241.

As will now be described in greater detail below, in the assembled configuration as illustrated in FIGS. 5A, 5D, and 5E, rotation of the luer tip 226 relative to the valve tube 232 can cause the valve member 220 of the luer connector 210 to move between the open position and the closed position. As mentioned above, in some embodiments, the seal 218 can exert a biasing force on the valve tube 232 that can cause the valve tube 232 to remain in contact with the luer tip 226. In particular, the seal 218 can cause the surface 232c of the valve tube 232 to abut against the surface 226c, as is illustrated in FIGS. 5A, 5D and 5E. In some embodiments, the luer connector 210 can be configured such that when the luer tip 226 is rotated, the valve tube 232 moves from an open to a closed, or from a closed to an open position, depending on the direction that the luer tip 226 is rotated. In particular, in some embodiments, the luer tip 226 can define an angled surface 226c that can have an ovular cross-section and the valve tube 232 can define an angled surface 232c that can also have an ovular cross-section. As with the other embodiments disclosed herein, in some embodiments, the luer tip 226 and the valve tube 232 can be manufactured at least in part from a rigid, medically neutral material such as plastic or metal. Preferably, rotation of the luer tip will cause the luer tip 226 and the valve tube 232 to translate relative to each other rather than deform and maintain their sealing relationship. As the luer tip 226 rotates in a first direction relative to the valve tube 232, the respective angled, ovular surfaces can cause the valve tube 232 to move toward the second end 214 of the luer connector 210. Similarly, when the valve tube 232 is an open position, as the luer tip 226 rotates in a second direction relative to the valve tube 232 that is opposite from the first direction, as the ovular shaped angled surface 232c of the valve tube 232 aligns with the ovular shaped angled surface 226c of the luer tip 226, the resilient seal 218 can cause the end portion of the valve tube 232 to become engaged with and, hence, substantially seal the opening 238 formed in the end portion of the luer tip 226.

Accordingly, the relative rotation of the luer tip 226 with respect to the valve tube 232 can cause the valve tube 232 to move between the opened and closed position. In some embodiments, the luer tip 226 can be configured so as to define rotational limits or stops arranged to ensure that, as a female connector 76 is threadedly engaged with the luer connector 210 as described in greater detail below, the luer tip 226 rotates to a desired radial position that causes the valve tube 232 to open a sufficient amount to permit fluid or medicament to flow through the luer connector 210. Similarly, the rotational limits or stops can be arranged to ensure that, as the female connector 76 is threadedly disengaged from the luer connector 210, the luer tip 226 rotates to a desired radial position allows the valve tube 232 to sealingly close against the inside surface of the luer tip 226 by the bias force provided by the resilient seal 218. In particular, in some embodiments, the luer tip 226 and the housing 222 can define splines, channels, protrusions, tabs, pins, or other indexing features configured to control the range of rotation of the luer tip 226 relative to the housing 222. When the luer connector 210 is in the closed position, the outer surface of the distal portion of the valve tube 232 can be sealingly closed against the inner surface of the distal portion 226a of the luer tip 226 such that fluid can be generally prevented from flowing through the opening 238 formed in the distal end portion of the luer tip 226.

As mentioned, in the illustrated embodiment, the tube 232 can be slidably supported so as to translate axially within the luer tip 226. Further, an annular sealing member 244 can be positioned between the outside surface of the valve tube 232 and the inside surface of the luer tip 226 to prevent fluid from flowing into the chamber 246. The sealing member 244 can comprise any of the materials, geometries, sizes, or other details of configurations of any other seal or a sealing member described herein. In some embodiments, the sealing member 244 can be formed from the same material as the valve tube 232 and can be formed integrally with the valve tube 232. In some embodiments, the sealing member 244 can be formed from a different material as compared to the valve tube 232 and can be sealably attached thereto. In some embodiments, the sealing member 244 can be formed separately from the valve tube 232 and positioned at the desired axial location of either the valve tube 232 or the inside surface of the luer tip 226. In some embodiments, either the inside surface of the luer tip 226 or the outside surface of valve tube 232 can comprise features such as channels or depressions to secure the sealing member 244 in the desired location.

In some embodiments, as mentioned, the seal 218 can be resilient and biased toward an expanded position, as illustrated in FIG. 5A, so as to exert a force on the valve tube 232 that biases the valve tube 232 toward the closed position. In particular, in the illustrated embodiment, the seal 218 can bias the valve tube 232 to sealably close against the inside surface of the luer tip 226. Further, the seal 218 can be configured so that the volume generally contained within the interior portion of the seal 218 when the valve member 220 is in the closed position (which is represented by V1 in FIG. 5A) can be greater than the volume contained within the interior portion of the seal 218 when the valve member 220 is in the open position (which is represented by V2 in FIG. 5D). Thus, the volume of fluid contained within the interior portion of the seal 218 can decrease when the valve member 220 moves from the closed position to the open position and can increase when the valve member 220 moves from the open position to the closed position. By increasing the volume of space within the seal 218 as the valve member 220 moves to the closed position, the seal 218 can create a force of suction that can reduce the amount of fluid or medicament that can flow through or drip out of the opening 238 as the valve member 220 is in the process of closing by drawing such fluid back into the volume of space within the interior of the seal 218.

Embodiments wherein seal 218 does not substantially enclose a volume, for example when seal 218 is a spring, function in a similar manner. Chamber 246 is configured so that its volume when the valve member 220 is in the closed position is greater than its volume when the valve member 220 is in the open position. The change in volumes can draw fluid from the first end 212 of the luer connector 210 into the connector 210 as the connector 210 moves from the open to the closed positions.

In some embodiments, the seal 218, the tube 232, and the sealing member 244 can all be integrally formed from the same material. In some embodiments, however, any of these features can be formed separately and supported or attached in the desired position as described above or in any other suitable manner. The housing 222 can generally be a tube-like structure with a passageway 254 that can extend from the second end 214 of the connector 210 through the axial center of the luer connector 210. As such, in some embodiments, when the luer connector 210 is in the open configuration as illustrated in FIG. 5B, the passageway 254 can permit fluid to flow from the second end 214 through the port member 224, the seal 218, the opening 264 in the tube 232, and out through the opening 238 in the luer tip 226 positioned at the first end 212 of the luer connector 210.

With reference to FIGS. 5A and 5D, near the second end 214 of the luer connector 210, the port member 224 and the corresponding section of the fluid passageway 254 can be sufficiently wide so as to accommodate a section of standard-diameter medical tubing or a standard male luer inserted therein. The length, diameter, or other features and of the housing 222 (or any housing described herein) can be the same as any other housing described herein.

Additionally, the shroud 228 can be sized and configured as described above or as desired to securely or removably attached the luer connector 210 to another medical implement. Further, the housing 222, tip 226, seal 218, or any other components or features of the luer connector 210 can have or be made from any of the materials, shapes, features, sizes, or other configurations or details described with regard to any other tip member disclosed herein. As with other embodiments of the luer tip, the luer tip 226 can be made to comply with applicable standards and/or regulations, such as the ANSI and/or ISO standards.

With reference to FIG. 5D, as the male luer connector 210 and female connector 76 move towards each other into threaded engagement, the inside surface 86 of the female connector 76 can contact the outside surface of the luer tip 226. This can cause a fluid tight seal between the inside surface 86 of the female connector 76 and the outside surface of the luer tip 226. As the male luer connector 210 and female connector 76 move further into threaded engagement, the contact force between the inside surface 86 of the female connector 76 and the outside surface of the luer tip 226 can cause the luer tip 226 to rotate substantially in unison with the female connector 76. This can cause in the luer tip 226 to rotate relative to the valve tube 232 as described above, causing the distal end portion 232a of the valve tube 232 to move away from the interior distal end portion 226a of the luer tip 226, as described above. As the valve tube 232 and luer tip 226 move apart from one another, a gap can form between the outside surface of the end portion of valve tube 232 and the inside surface of the end portion of the luer tip 226, permitting fluid to pass through the opening 238 into the fluid passageway 80 of the female connector 76, or vice versa.

As discussed above, as the valve tube 232 opens and causes the seal 218 to be compressed, the volume of fluid that can be contained within the seal 218 can decrease. In some embodiments, when a constant source of positive pressure is imparted on the passageway 254 at the second end 214 of the luer connector 210, while the seal 218 is being compressed (which decreases the volume of fluid in the seal 218), the fluid within the seal 218 will be subjected to an increased pressure due to the compression of the seal 218. In some embodiments, this increased pressure can cause the fluid within the seal 218 to flow through the passageway 254 toward the first end 212 of the luer connector 210 at an increased rate, until the seal 218 is no longer being compressed.

Conversely, in some embodiments, when the female connector 76 is removed from the luer connector 210, the interaction between the inside surface 86 of the female connector 76 and the outside surface of the luer tip 226 can cause the luer tip 226 to rotate relative to the valve tube 232, causing the valve tube 232 to move to the closed position relative to the luer tip 226. As the valve tube 232 moves toward the closed position, the volume within the seal 218 can increase back to volume V1. The expansion of the interior volume of the seal 218 can cause a reduced pressure or suction to be generated within the seal 218. As mentioned, this reduced pressure or suction can cause the luer connector 210 to draw at least some of the fluid that is within the opening 264 back into the volume of space within the seal 218. In some embodiments, the luer connector 210 may be used to control the flow of fluids or medicaments that are harmful or corrosive, such that preventing even a few drops from dripping out of the opening 238 as the female connector 76 is being removed can be beneficial.

Figure 6F:
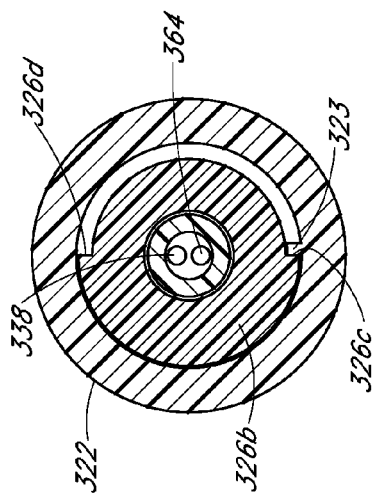
FIG. 6F is a cross-sectional view of the embodiment of the luer connector shown in FIG. 6A taken through line 6F-6F and in FIG. 6A.
Figure 6G:
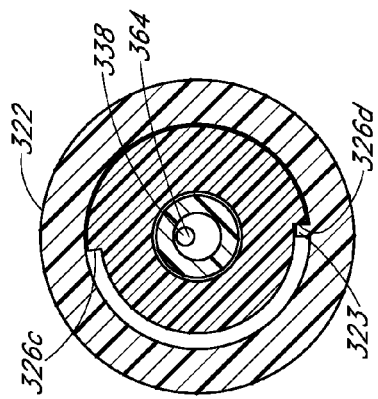
FIG. 6G is a cross-sectional view of the embodiment of the luer connector shown in FIG. 6A taken through line 6G-6G and in FIG. 6B.
Figure 6E:
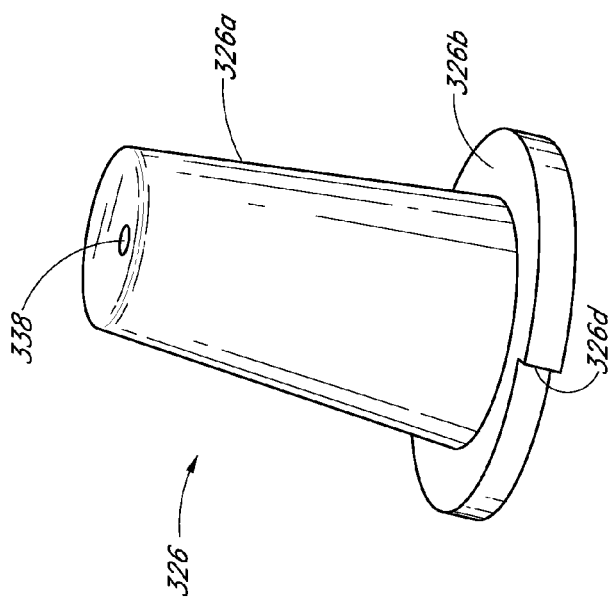
FIG. 6E is a perspective view of an embodiment of a luer tip of the embodiment of the luer connector shown in FIG. 6A.

Referring now to FIGS. 6A-6G, another embodiment of a closeable luer connector 310 will be described. FIG. 6A is a cross-sectional view of the luer connector 310, showing the luer connector 310 in a first or closed position. FIG. 6B is a cross-sectional view of the luer connector 310, showing the luer connector 310 in a second or open position. FIG. 6C is an end view of the embodiment of the luer connector 310, showing the luer connector 310 in a closed position. FIG. 6D is an end view of the luer connector 310, showing the luer connector 310 in an open position. FIG. 6E is a perspective view of an embodiment of a luer tip 326. FIG. 6F is a cross-sectional view of the luer connector 310 taken through line 6F-6F and in FIG. 6A, showing the luer connector 310 in a closed position. FIG. 6G is a cross-sectional view of the luer connector 310 taken through line 6G-6G and in FIG. 6B, showing the luer connector 310 in an open position.

In some embodiments, the luer connector 310 can have or be made from any of the components, features, materials, sizes, geometries, details, or configurations of any of the other luer connectors disclosed herein. FIG. 6A is a cross-sectional view of the luer connector 310 in a closed position so that fluid is generally prevented from flowing through the luer connector 310. FIG. 6B is a cross-sectional view of the embodiment of the luer connector 310 in an open position due to the engagement of a female connector 76 with the luer connector. The flow of fluid or medicament through the luer connector 310 is represented by arrows in FIG. 6B. As described above with reference to other luer connectors, when the valve tube 332 (also referred to as an internal member) of the luer connector 310 is in the open position, fluid can be generally permitted to flow through the luer connector 310. Similarly, when the valve tube 332 is in a closed position, fluid can be generally prevented from flowing through the luer connector 310. As with any embodiment of the luer connector described herein, a perfect seal by the valve member is not required, although such a seal may be preferred in some embodiments.

In some embodiments, the luer connector 310 can be the same or similar to the luer connector 210 described above, except for or in addition to the features and components illustrated and/or described below. Accordingly, in some respects, the luer connector 310 can operate in the same or similar manner as compared to the luer connector 210 described above. As illustrated in FIG. 6A, some embodiments of the assembled luer connector 310 can comprise a housing 322, a port member 324 positioned near the second end 314 of the luer connector 310, a luer tip 326 positioned near the first end 312 of the luer connector 310, a shroud 328 surrounding at least a portion of the luer tip 326, and a valve member 320. As illustrated, the valve tube 332 can be integrally formed with the housing 322, or can be separately formed and attached to the housing 322 by any of the bonding or fusing techniques described in this disclosure or known in the art. The luer tip 326 can be supported within the housing 322. In the illustrated embodiment, the valve member 320 can comprise a luer tip 326 and a valve tube 332. In some embodiments, the valve tube 332 can be positioned at least partially within the opening 360 that can be formed in the luer tip 326.

In some embodiments, as in the illustrated embodiment, the housing 322 can define an opening 340 through which the luer tip 326 can project. With reference to FIG. 6A, the luer connector 310 can be configured so that the luer tip 326 projects toward the first end 312 of the luer connector 310. The luer tip 326 is preferably co-axially aligned with the centerline of the housing 322, port member 324, and the shroud 328. The opening 340 can be sized and configured so as to provide radial support to the luer tip 326 so that the luer tip 326 remains generally co-axially aligned with the centerline of the housing 322. The opening 340 can be sized and configured so as to not restrict the rotation of the luer tip 326 relative to the housing 322. The luer connector 310 also can be configured so that the luer tip 326 is axially supported within the housing 322. Additionally, for reasons that will be described in greater detail below, the housing 322 and opening 340 can be sized and configured so that the luer tip 326 can freely rotate within a predetermined angular range relative to the housing 322, the shroud 328, and the valve tube 332.

With reference to FIG. 6E, in some embodiments, the luer tip 326 can be formed so as to define a generally conical, tapered outside surface 326a projecting from a planar base portion 326b toward the first end 312 of the luer connector 310. With reference to FIG. 6F, in some embodiments, the planar base portion 326b can be formed so as to define a first abutment surface 326c and a second abutment surface 326d. Additionally, in some embodiments, the housing 322 can define a protrusion or tab 323 that can be generally longitudinally aligned with the first and second abutment surfaces 326c, 326d. As will be described in greater detail below, the tab 323 and the first and second abutment surfaces 326c, 326d can be configured to define or limit the angular range of rotation between the luer tip 326 and the housing 322. The luer tip 326 can also be configured to define a generally cylindrical opening 360 through at least a portion of the luer tip 326, with the opening 360 being generally aligned with the axial centerline of the luer tip 326.

In some embodiments, the valve tube 332 can be formed so as to define a generally cylindrical outside surface 332a that is sized and configured to be received within a generally cylindrically shaped opening 360 that can be formed in the luer tip 326. The outside surface 332a of the valve tube 332 can project from the housing 322 toward the first end 312 of the luer connector 310.

As mentioned, the luer tip 326 can be axially and radially supported by the housing 322 in a manner that permits the luer tip 326 to rotate substantially freely relative to the housing 322 in response to coupling to another connector or other manipulation, preferably within a defined angular range, but in a manner that substantially prevents axial movement of the luer tip 326 relative to the housing 322. As illustrated in other embodiments, opening 340 may include a resilient seal, for example an o-ring, which engages the rotating luer tip 326. In some embodiments, the port member 324 can be adhered, fused, welded, or otherwise attached to the housing 322 along the part line surface 325 after the luer tip 326 has been assembled within the housing 322. In some embodiments, the housing 322 can define additional or different part lines so that all of the internal components such as the valve tube 332, the seal 318, and the valve tube 326, and can be assembled therein.

As will now be described in greater detail below, in the assembled configuration, as illustrated in FIGS. 6A and 6B, rotation of the luer tip 326 relative to the valve tube 332 can cause the valve member 320 of the luer connector 310 to move between a second, open position and a first, closed position. In the open position, as illustrated in FIGS. 6B and 6D, the opening 338 in the luer tip 326 is generally aligned with the opening 364 in the valve tube 332. In the closed position, as illustrated in FIGS. 6A and 6C, the opening 338 in the luer tip 326 is generally out of alignment with respect to the opening 364 in the valve tube 332. In some embodiments, the luer connector 310 can be configured such that, when the luer tip 326 is rotated, the valve tube 332 moves from an open to a closed position, or from a close to an open position, depending on the direction that the luer tip 326 is rotated. The first and second abutment surfaces 326c, 326d can be configured so as to stop the rotation of the luer tip 326 in either a first or second direction so that the luer tip 326 is either aligned in an open position or a closed position relative to the valve tube 332 at the stop positions.

Accordingly, the relative rotation of the luer tip 326 with respect to the valve tube 332 can cause the valve member 320 to move between the opened and closed position. As mentioned, in some embodiments, the luer tip 326 can be configured so as to define a rotational limits or stops arranged to ensure that, as a female connector 76 is threadedly engaged with the luer connector 310 as described in greater detail below, the luer tip 326 rotates to a desired angular orientation that causes the valve tube 332 to open a sufficient amount to permit fluid or medicament to flow through the luer connector 310. Similarly, the rotational limits or stops can be arranged to ensure that, as the female connector 76 is threadedly disengaged from the luer connector 310, the luer tip 326 rotates to a desired radial position allows the valve tube 332 to sealingly close against the inside surface of the luer tip 326.

An annular sealing member 344 can be positioned between the outside surface of the valve tube 332 and the inside surface of the luer tip 326 to prevent fluid from flowing through the opening 360 toward the base portion 326b of the luer tip 326 and out through the opening 340. The sealing member 344 can comprise any of the materials, geometries, sizes, or other details or configurations of any other seal or a sealing member described herein. In some embodiments, the sealing member 344 can be formed from the same material as the valve tube 332 or the luer tip 326 and can be formed integrally with the valve tube 332 or the luer tip 326. In some embodiments, the sealing member 344 can be formed independently and can be sealably attached to either the valve tube 332 or the luer tip 326. In some embodiments, the sealing member 344 can be formed separately from the valve tube 332 and positioned at the desired axial location of either the valve tube 332 or the inside surface of the luer tip 326. In some embodiments, either the inside surface of the luer tip 326 or the outside surface of valve tube 332 can comprise features such as channels or depressions to secure the sealing member 344 in the desired location.

The housing 322 can be generally a tube-like structure with a passageway 354 that can extend from the second end 314 of the connector 310 through the axial center of the luer connector 310. As such, in some embodiments, when the luer connector 310 is in the open configuration as illustrated in FIG. 6B, the passageway 354 can permit fluid to flow from the second end 314 through the port member 324, the seal 318, the opening 364a in the tube 332, and out through the opening 338 in the luer tip 326 positioned at the first end 312 of the luer connector 310. The length, diameter, or other features of the housing 32 can be the same as any other housing described herein.

Additionally, the shroud 328 can be sized and configured as described above or as desired to securely or removably attached the luer connector 310 to another medical implement. Further, the housing 322, tip 326, seal 318, or any other components or features of the luer connector 310 can have or be made from any of the materials, shapes, features, sizes, or other configurations or details described with regard to any other tip member disclosed herein. As with other embodiments of the luer tip, the luer tip 326 can be made to comply with applicable standards and/or regulations, such as the ANSI and/or ISO standards.

With reference to FIG. 6B, as the male luer connector 310 and female connector 76 move towards each other into threaded engagement, the inside surface 86 of the female connector 76 can contact the outside surface of the luer tip 326. This can cause a fluid tight seal between the inside surface 86 of the female connector 76 and the outside surface of the luer tip 326. As the male luer connector 310 and female connector 76 move further into threaded engagement, the contact force between the inside surface 86 of the female connector 76 and the outside surface of the luer tip 326 can cause the luer tip 326 to rotate substantially in unison with the female connector 76. This can cause in the luer tip 326 to rotate relative to the valve tube 332 as described above, causing the opening 338 in the luer tip 326 to move relative to the opening 364 in the valve tube 332, as described above.

In some embodiments, the luer connector 310 can be configured to substantially prevent accidental rotational movement of the luer tip 326 from the first, closed position to prevent accidental opening of the connector 310 and, consequently, accidental discharge of fluid in the luer connector 310. For example, some embodiments of the luer connector 310 can have detents, notches, tabs, resilient members, or other features that inhibit the rotational movement of the luer tip 326 relative to the valve tube 332.

Figure 7A:
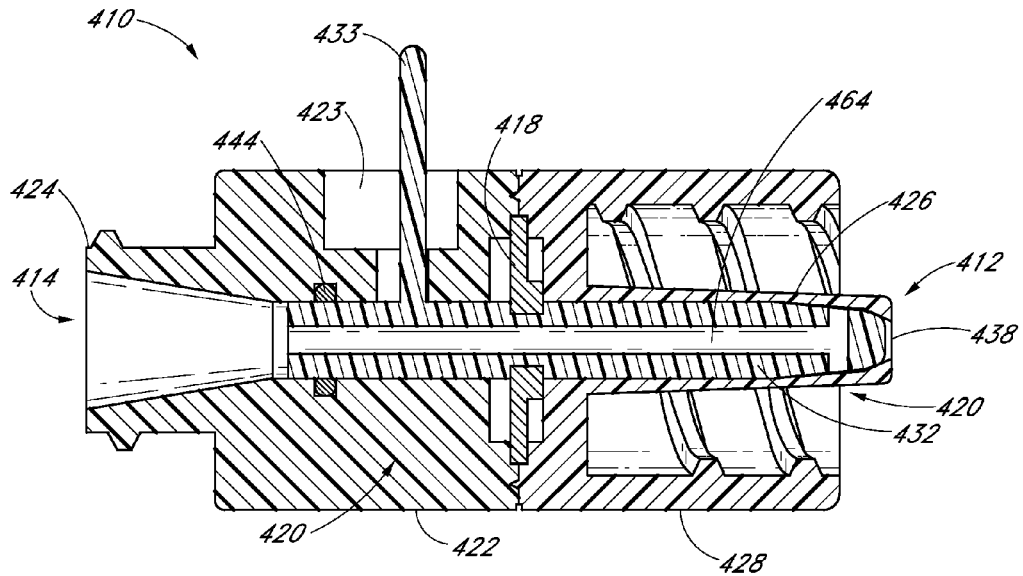
FIG. 7A is a cross-sectional view of another embodiment of a luer connector in a closed position.
Figure 7B:
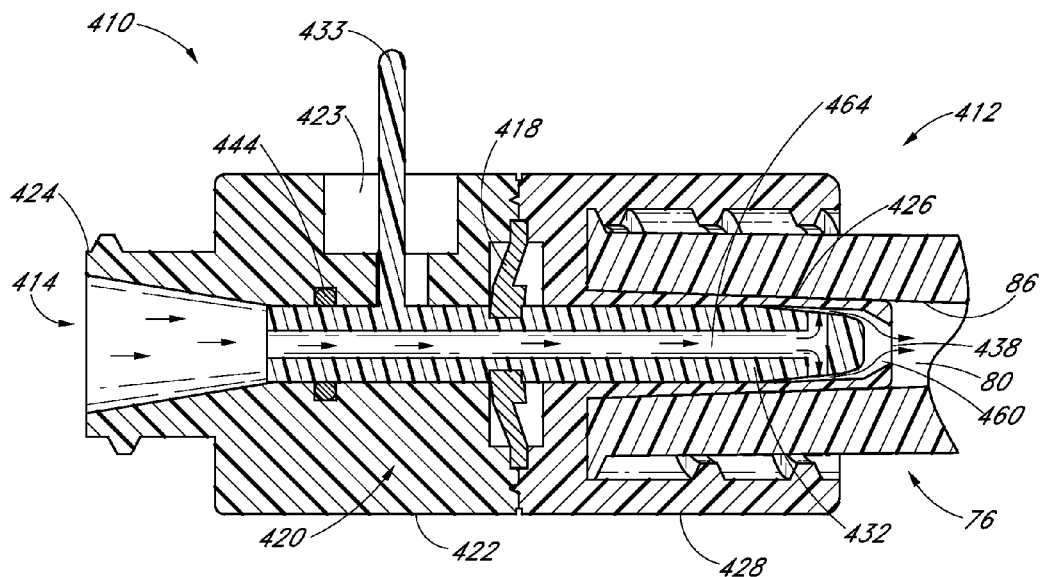
FIG. 7B is a cross-sectional view of the embodiment of the luer connector shown in FIG. 7A in an open position.

Referring now to FIGS. 7A-7B, another embodiment of a closeable luer connector 410 will be described. In some embodiments, the luer connector 410 can have or be made from any of the components, features, materials, sizes, geometries, details, or configurations of any of the other luer connectors disclosed herein. FIG. 7A is a cross-sectional view of the luer connector 410, showing the luer connector 410 in a closed position so that fluid is generally prevented from flowing through the luer connector 410. FIG. 7B is a cross-sectional view of the luer connector 410, showing the luer connector 410 in an open position so that fluid is generally permitted to flow through the luer connector 410. As will be described, in some embodiments, the luer connector 410 can be configured so that the luer connector 410 is manually changed between an open and a closed position, and is not automatically changed to an open position when the luer connector 410 is engaged with a female connector. The flow of fluid or medicament through the luer connector 410 is represented by arrows in FIG. 7B. As with any embodiment of the luer connector described herein, a perfect seal by the valve member is not required, although such a seal may be preferred in some embodiments.

In some embodiments, the luer connector 410 can be the same or similar to the luer connector 10 described above, except for or in addition to the features and components illustrated in FIGS. 7A and 7B, and/or described below. Accordingly, in some respects, the luer connector 410 can operate in the same or similar manner as compared to the luer connector 10 described above. As illustrated in FIG. 7A, some embodiments of the assembled luer connector 410 can comprise a housing 422, a port member 424 positioned near the second end 414 of the luer connector 410, a luer tip 426 positioned near the first end 412 of the luer connector 410, a shroud 428 surrounding at least a portion of the luer tip 426, and a valve member 420. As illustrated, the luer tip 426 can be integrally formed with the housing 422 or, in some embodiments, the luer tip 426 can be separately formed and attached to the housing 422 by any of the bonding or fusing techniques described herein or known in the art.

In the illustrated embodiment, the valve member 420 can comprise the luer tip 426, a valve tube 432 (also referred to as an internal member) supported within the luer tip 426, and a handle 433. In some embodiments, the valve tube 432 and the handle 433 can be integrally formed. In some embodiments, the handle 433 can be separately formed as compared to the valve tube 432 and attached to the valve tube 432 by any of the bonding or fusing techniques described in herein or known in the art. In some embodiments, the valve tube 432 can be positioned at least partially within the opening 460 that can be formed in the luer tip 426.

Similar to other luer connectors described herein, the end portion of the valve tube 432 can be configured to create a substantially fluid tight seal with respect to the luer tip 426 when the valve member 420 is in the closed position. Additionally, when the valve member 420 is in the open position, fluid can be permitted to flow through the opening 464 formed in the valve tube 432 and out through the opening 438 formed in the luer tip 426. In some embodiments, the valve member 420 can be moved between the opened and closed positions by manually exerting a force on the handle 433 that can project through an opening or openings 423 in the housing 422. In particular, the valve member 420 can be opened by moving the handle 433 toward the second end 414 of the luer connector 410. Similarly, the valve member 420 can be closed by moving the handle 433 toward the first end 412 of the luer connector 410.

In some embodiments, the resilient seal member 418 can be supported by the housing 422 and configured to create a fluid tight seal around the outside surface of a portion of the valve tube 432. Additionally, the resilient seal number 418 can be configured to exert a biasing force on the valve tube 432 that biases the valve member 420 to the closed position. In some embodiments, the resilient seal member 418 can define a substantially planar, annular shape, having a circular opening therein that can constrict around the outside surface of a portion of the valve tube 432. An additional seal 444 can be positioned around a portion of the valve tube 432 near the second end 414 of the luer connector to substantially prevent fluid from leaking through the opening or openings 423 and the housing 422.

In some embodiments, the valve tube 432 and/or the housing 422 can be configured to define detents, stops, or other features to cause the valve member 420 to remain in the open or partially open position against the biasing force of the seal member 418, after the user has moved the valve member 420 to the open position. This can allow the valve member 420 to remain in the open position without requiring the user to hold the handle 433 in the open position. In some embodiments, exerting a force on the handle member in the direction of the first end 412 of the luer connector 410 can cause the valve member 420 to close. In some embodiments, the valve tube 432 and the housing 422 can be configured so that the user can hold the handle 433 in the open position to cause the valve member 420 to remain open.

Figure 8A:
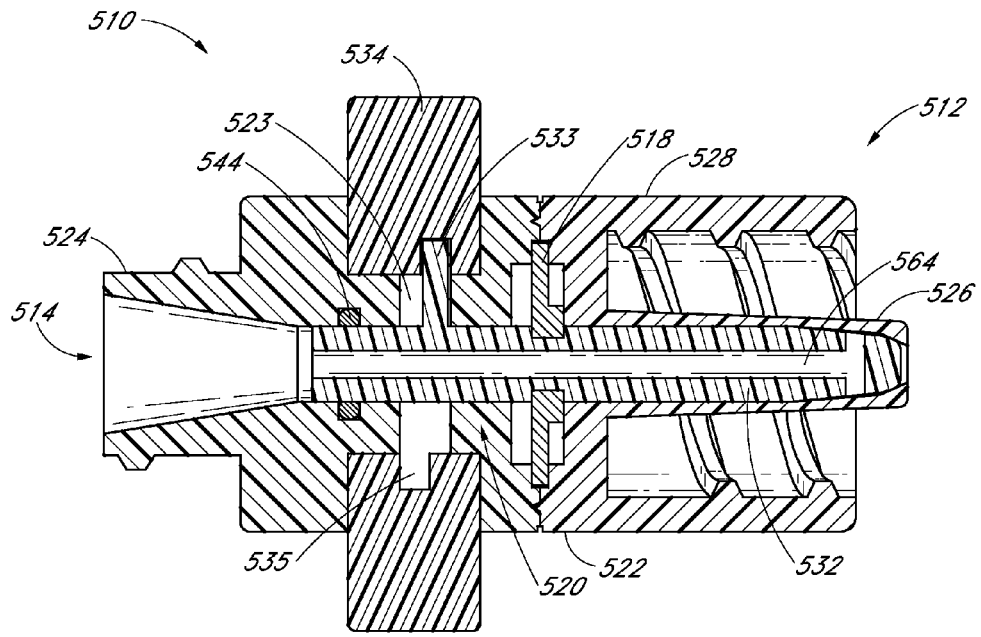
FIG. 8A is a cross-sectional view of another embodiment of a luer connector in a closed position.
Figure 8B:
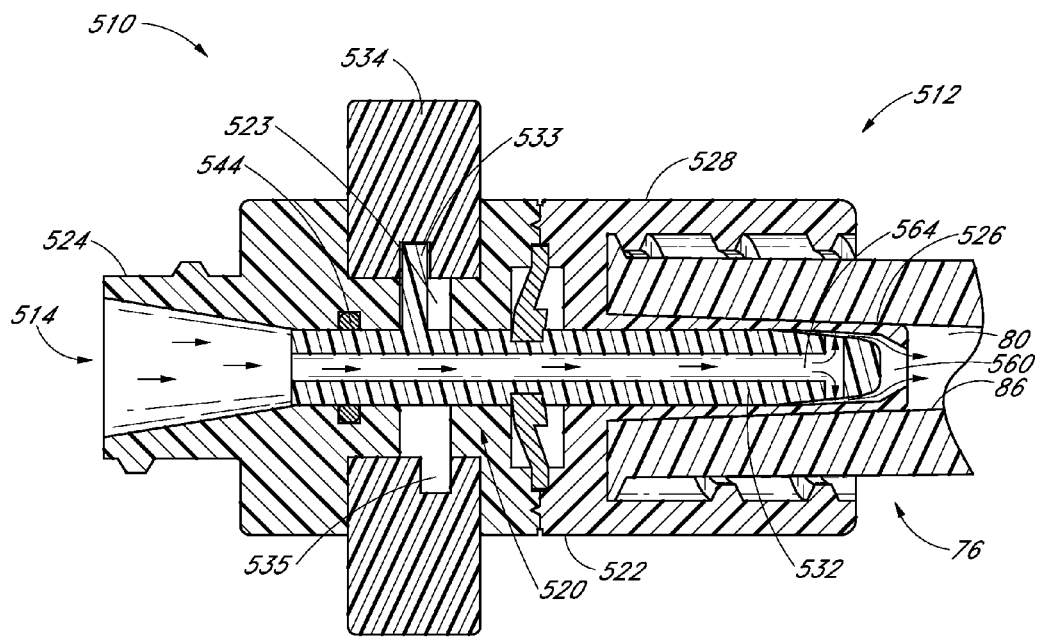
FIG. 8B is a cross-sectional view of the embodiment of the luer connector shown in FIG. 8A in an open position.

Referring now to FIGS. 8A-8B, another embodiment of a closeable luer connector 510 will be described. In some embodiments, the luer connector 510 can have or be made from any of the components, features, materials, sizes, geometries, details, or configurations of any of the other luer connectors disclosed herein. FIG. 8A is a cross-sectional view of the luer connector 510, showing the luer connector 510 in a closed position so that fluid is generally prevented from flowing through the luer connector 510. FIG. 8B is a cross-sectional view of the luer connector 510, showing the luer connector 510 in an open position so that fluid is generally permitted to flow through the luer connector 510. As will be described, in some embodiments, the luer connector 510 can be configured so that the luer connector 510 is manually changed between an open and a closed position, and is not automatically changed to an open position when the luer connector 510 is engaged with a female connector. The flow of fluid or medicament through the luer connector 510 is represented by arrows in FIG. 8B. As with any embodiment of the luer connector described herein, a perfect seal by the valve member is not required, although such a seal may be preferred in some embodiments.

In some embodiments, the luer connector 510 can be the same or similar to the luer connector 410 described above, except for or in addition to the features and components illustrated in FIGS. 8A and 8B and/or described herein. Accordingly, in some respects, the luer connector 510 can operate in the same or similar manner as compared to the luer connector 410 described above. As illustrated in FIG. 8A, some embodiments of the assembled luer connector 510 can comprise a housing 522, a port member 524 positioned near the second end 514 of the luer connector 510, a luer tip 526 positioned near the first end 512 of the luer connector 510, a shroud 528 surrounding at least a portion of the luer tip 526, and a valve member 520. As illustrated, the luer tip 526 can be integrally formed with the housing 522 or, in some embodiments, the luer tip 526 can be separately formed and attached to the housing 522 by any of the bonding or fusing techniques described herein or known in the art.

In the illustrated embodiment, the valve member 520 can comprise the luer tip 526, a valve tube 532 (also referred to as an internal member) supported within the luer tip 526, a protrusion or tab 533, and a dial member 534. In some embodiments, the valve tube 532 and the tab 533 can be integrally formed. In some embodiments, the tab 533 can be separately formed as compared to the valve tube 532 and attached to the valve tube 532 by any of the bonding or fusing techniques described herein or known in the art. The valve tube 532 can be positioned at least partially within the opening 560 that can be formed in the luer tip 526. In some embodiments, the valve tube 532 and the housing 522 can be configured to permit the valve tube 532 to translate axially within a predetermined range relative to the housing 522 so that the valve tube 532 can move between the open and closed positions. Additionally, the valve tube 532 and the housing 522 can define channels, notches, protrusions, indexing features, or otherwise be configured to substantially prevent the valve tube 532 from rotating relative to the housing 522.

Similar to other luer connectors described herein, the end portion of the valve tube 532 can be configured to create a substantially fluid tight seal with respect to the luer tip 526 when the valve member 520 is in the closed position. Additionally, when the valve member 520 is in the open position, fluid can be permitted to flow through the opening 564 formed in the valve tube 532 and out through the opening 538 formed in the luer tip 526. In some embodiments, the valve member 520 can be moved between the opened and closed positions by manually exerting a force on the tab 533 that can project through an opening or series of openings 523 in the housing 522. In particular, the valve member 520 can be opened by moving the tab 533 toward the second end 514 of the luer connector 510, as will be described below. Similarly, the valve member 520 can be closed by moving the tab 533 toward the first end 512 of the luer connector 510.

In some embodiments, the resilient seal member 518 can be supported by the housing 522 and configured to create a fluid tight seal around the outside surface of a portion of the valve tube 532. Additionally, the resilient seal number 518 can be configured to exert a biasing force on the valve tube 532 that biases the valve member 522 to the closed position. In some embodiments, the resilient seal member 518 can define a substantially planar, annular shape, having a circular opening therein that can constrict around the outside surface of a portion of the valve tube 532. An additional seal 544 can be positioned around a portion of the valve tube 532 near the second end 514 of the luer connector to substantially prevent fluid from leaking through the opening or series of openings 523 and the housing 522.

In some embodiments, the dial member 534 can be formed from two or more pieces and snapped together or otherwise joined together around the housing 522 and the tab 533. The dial member 534 can be supported by the housing 522 in a manner that allows the dial to freely rotate relative to the housing 522 and the valve tube 532, while being axially supported by the housing 522 so that the dial member 534 is substantially prevented from translating in either axial direction relative to the housing 522. Additionally, the dial member 534 and/or the housing 522 can be configured to define detents, stops, or other features to bias or stop the dial member 534 at particular predetermined locations corresponding to desired positions of the valve member 520 such as, but not limited to, open, closed, and priming positions.

In some embodiments, the dial member 534 can define a helically shaped channel 535 configured to slidingly receive the tab 533. In this configuration, in some embodiments, because the valve tube 532 and tab 533 are substantially prevented from rotating relative to the housing, as the dial 534 is rotated, the helical shape of the channel 535 can cause the tab 533 and, hence, the valve tube 532, to move in either axial direction relative to the housing, depending on the direction that the dial 534 is rotated. In this manner, the valve member 520 can be caused to be moved between open and closed positions.

In some embodiments, as mentioned, the dial member 534 and/or the housing 522 can be configured to define detents, stops, or other features to cause the valve member 520 to remain in the open or partially open position against the biasing force of the seal member 518, after the user has moved the valve member 520 to the open position. This can allow the valve member 520 to remain in the open position without requiring the user to hold the dial member 534 in the desired position.

Figure 9A:
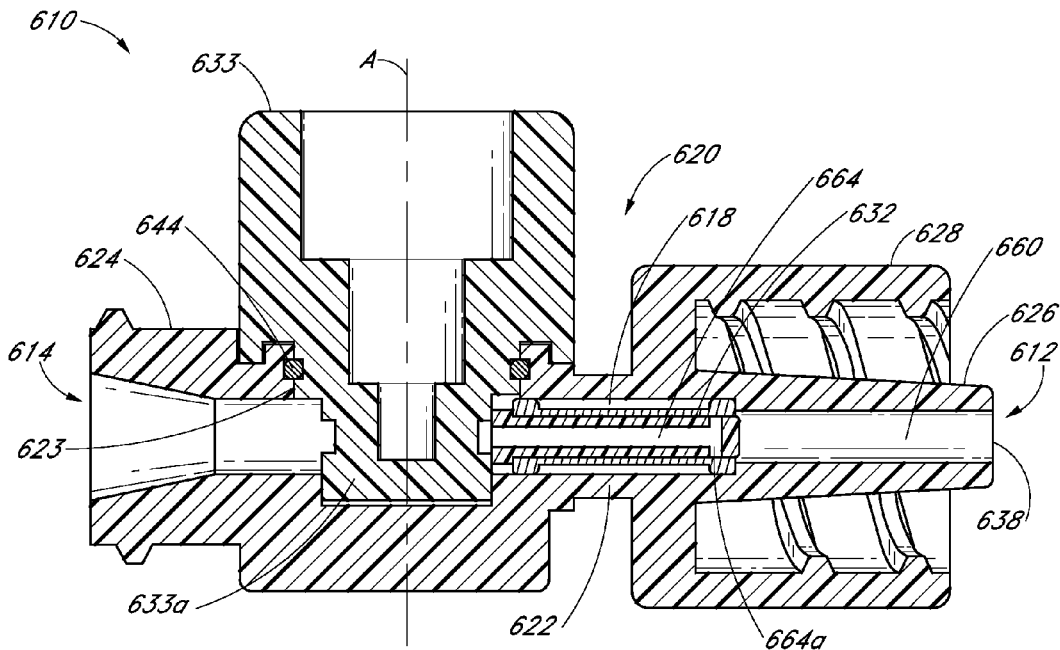
FIG. 9A is a cross-sectional view of another embodiment of a luer connector in a closed position.
Figure 9B:
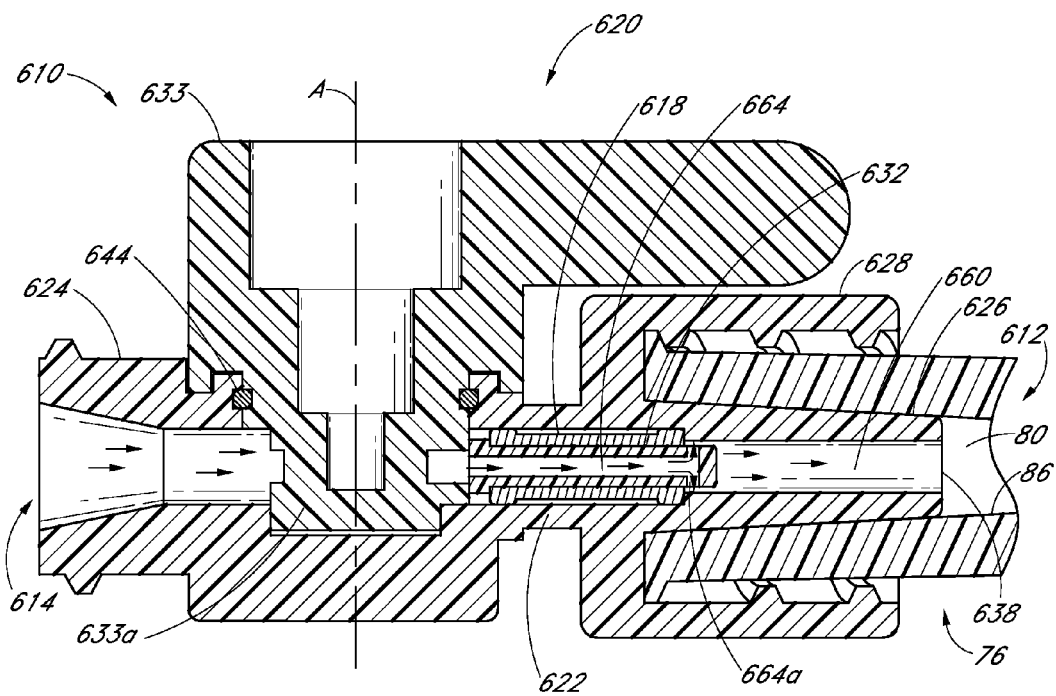
FIG. 9B is a cross-sectional view of the embodiment of the luer connector shown in FIG. 9A in an open position.

Referring now to FIGS. 9A-9B, another embodiment of a closeable luer connector 610 will be described. In some embodiments, the luer connector 610 can have or be made from any of the components, features, materials, sizes, geometries, details, or configurations of any of the other luer connectors disclosed herein. FIG. 9A is a cross-sectional view of the luer connector 610, showing the luer connector 610 in a closed position so that fluid is generally prevented from flowing through the luer connector 610. FIG. 9B is a cross-sectional view of the luer connector 610, showing the luer connector 610 in an open position so that fluid is generally permitted to flow through the luer connector 610. As will be described, in some embodiments, the luer connector 610 can be configured so that the luer connector 610 is manually changed between an open and a closed position, and is not automatically changed to an open position when the luer connector 610 is engaged with a female connector. The flow of fluid or medicament through the luer connector 610 is represented by arrows in FIG. 9B. As with any embodiment of the luer connector described herein, a perfect seal by the valve member is not required, although such a seal may be preferred in some embodiments.

In some embodiments, the luer connector 610 can be the same or similar to the luer connector 510 described above, except for or in addition to the features and components illustrated in FIGS. 9A and 9B and/or described below. Accordingly, in some respects, the luer connector 610 can operate in the same or similar manner as compared to the luer connector 510 described above. As illustrated in FIG. 9A, some embodiments of the assembled luer connector 610 can comprise a housing 622, a port member 624 positioned near the second end 614 of the luer connector 610, a luer tip 626 positioned near the first end 612 of the luer connector 610, a shroud 628 surrounding at least a portion of the luer tip 626, and a valve member 620. As illustrated, the luer tip 626 can be integrally formed with the housing 622 or, in some embodiments, the luer tip 626 can be separately formed and attached to the housing 622 by any of the bonding or fusing techniques described herein or known in the art.

In the illustrated embodiment, the valve member 620 can comprise the luer tip 626, a valve tube 632 (also referred to as an internal member) supported within the luer tip 626, and a stopcock or handle member 633. The valve tube 632 can be positioned at least partially within the opening 660 that can be formed in the luer tip 626. In some embodiments, the luer connector 610 can be configured to permit the valve tube 632 to translate axially within a predetermined range relative to the housing 622 and luer tip 626 so that the valve tube 632 can move between the open and closed positions.

A generally cylindrically shaped, resilient sealing member 618 can be supported within the housing 622 and/or luer tip 626. The sealing member 618 can be configured to sealingly cover the opening or openings 664a of the passageway 664 in the valve tube 632 so that, when the valve tube 632 is in the closed position as illustrated in FIG. 9A, the sealing member 618 substantially prevents any fluid or medicament from flowing out of the opening or openings 664a formed in the valve tube 632. Further, the sealing member 618 can be sized and configured to permit fluid or medicament to flow through the opening or openings 664a in the valve tube 632 and out through the opening 638 in the luer tip 626 when the valve member 620 is in the open position.

Additionally, the sealing member 618 can be supported within the housing 622 and configured to exert a biasing force on the valve tube 632 that biases the valve tube 632 to the closed position. In particular, the sealing member 618 can be supported by the luer tip 626 and/or housing 622 so that the sealing member 618 is in at least a slightly compressed state, so as to exert a biasing force on the valve tube 632 in the direction of the second end 614 of the luer connector 610. When the handle 633 is moved to the open position, as illustrated in FIG. 9B, the valve tube 632 can be moved toward the first end 612 of the luer connector 610 against the biasing force of the sealing member 618. As the handle 633 is moved from the open position to the closed position (illustrated in FIG. 9A), the biasing force of the sealing member 618 can restore the valve tube 632 to the closed position, preventing additional fluid from flowing through the valve member 620. In some embodiments, fluid can flow around the base of the handle 633 in either the open or closed position. An additional seal 644 can be positioned around a portion of the valve tube 632 near the second end 614 of the luer connector to substantially prevent fluid from leaking through the opening or series of openings 623 and the housing 622.

In some embodiments, the handle 633 can be supported by the housing 622 in a manner that allows the handle to rotate substantially freely relative to the housing 622 and the valve tube 632, while being supported by the housing 622 so that the handle 633 does not become inadvertently detached from the housing 622. Additionally, the handle 633 and/or the housing 622 can be configured to define detents, stops, or other features to bias or stop the handle 633 at particular rotational positions corresponding to desired positions of the valve member 620 such as, but not limited to, open, closed, and priming positions.

The base portion 633a of the handle 633 can define an ovular or otherwise non-circular cross-section or otherwise be configured so as to axially displace the valve tube 632 as the handle 633 is turned. As such, the radial distance from the axial centerline or center of rotation (represented by the axis A in FIGS. 9A and 9B) to the surface of the base portion 633a can vary from one point to another on the surface of the base portion 633a. In particular, in some embodiments, the distance between the center of rotation A to the point on the surface of the base portion 633a in contact with the valve tube 632 when the valve tube 632 is in the open position (as illustrated in FIG. 9B) can be greater than the distance between the center of rotation A to the point on the surface of the base portion 633a in contact with the valve tube 632 when the valve tube 632 is in the closed position (as illustrated in FIG. 9A). In this configuration, the valve member 620 can be moved between the open and closed position by rotating the handle 633 relative to the housing 622, thus causing the valve 620 to move between the opened and closed position.

In some embodiments, as mentioned, the handle 633 and/or the housing 622 can be configured to define detents, stops, or other features to cause the valve member 620 to remain in the open or partially open position against the biasing force of the seal member 618, after the user has moved the valve member 620 to the open position. This can allow the valve member 620 to remain in the open position without requiring the user to hold the handle 633 in the desired position.

Figure 10A:
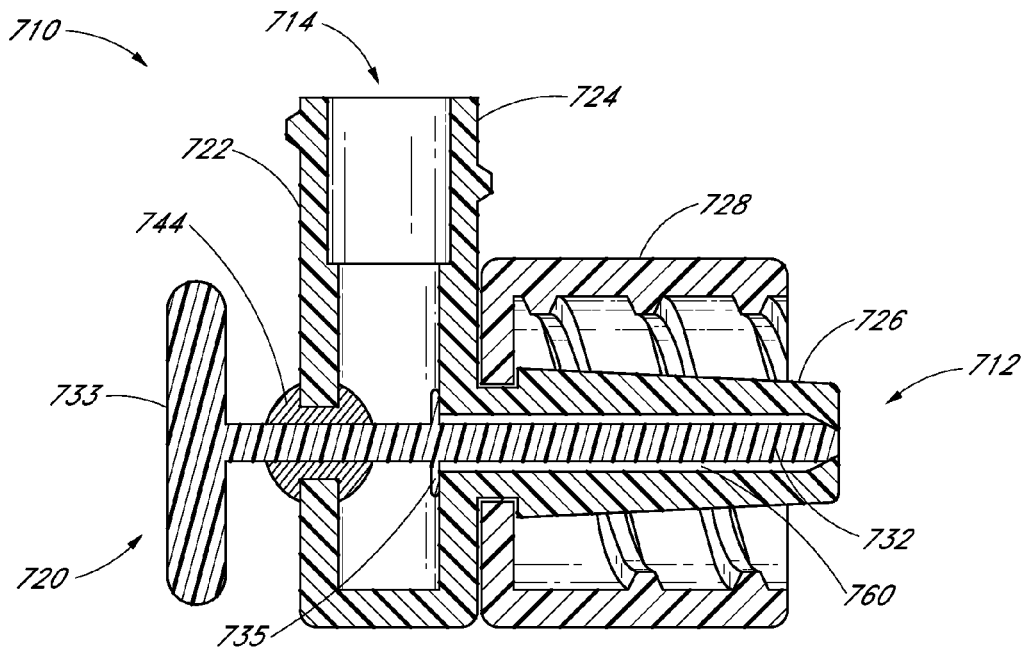
FIG. 10A is a cross-sectional view of another embodiment of a luer connector in a closed position.
Figure 10B:
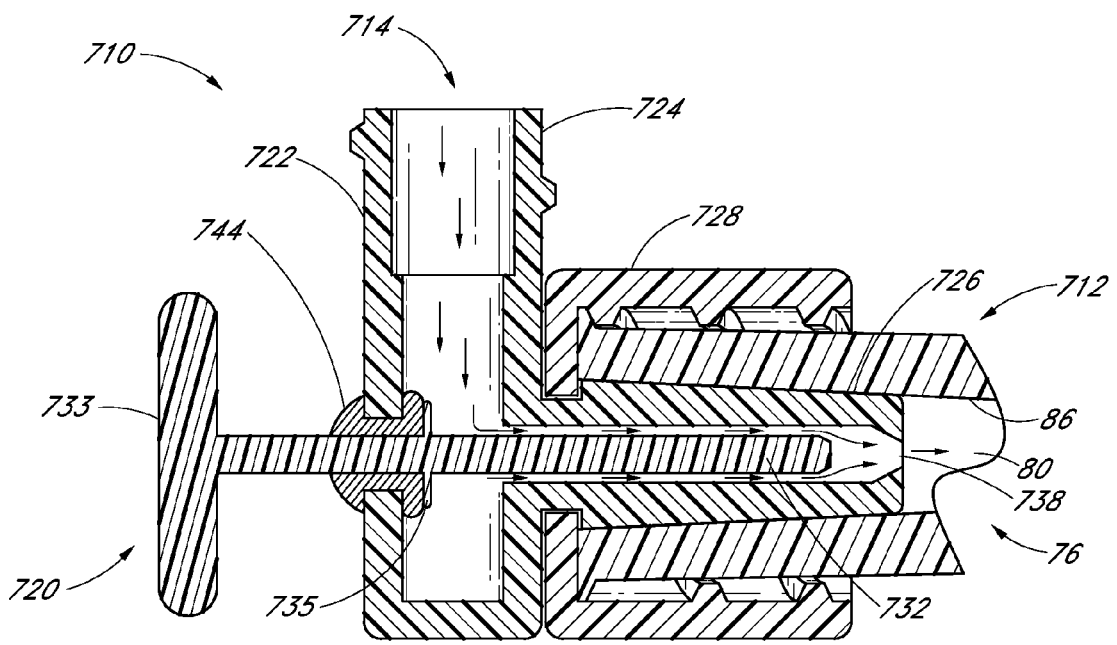
FIG. 10B is a cross-sectional view of the embodiment of the luer connector shown in FIG. 10A in an open position.

Referring now to FIGS. 10A-10B, another embodiment of a closeable luer connector 710 will be described. In some embodiments, the luer connector 710 can have or be made from any of the components, features, materials, sizes, geometries, details, or configurations of any of the other luer connectors disclosed herein. FIG. 10A is a cross-sectional view of the luer connector 710, showing the luer connector 710 in a closed position so that fluid is generally prevented from flowing through the luer connector 710. FIG. 10B is a cross-sectional view of the luer connector 710, showing the luer connector 710 in an open position so that fluid is generally permitted to flow through the luer connector 710. As will be described, in some embodiments, the luer connector 710 can be configured so that the luer connector 710 is manually changed between an open and a closed position, and is not automatically changed to an open position when the luer connector 710 is engaged with a female connector. The flow of fluid or medicament through the luer connector 710 is represented by arrows in FIG. 10B. As with any embodiment of the luer connector described herein, a perfect seal by the valve member is not required, although such a seal may be preferred in some embodiments.

In some embodiments, the luer connector 710 can be the same or similar to the luer connector 10 described above, except for or in addition to the features and components illustrated in FIGS. 10A and 10B and/or described below. Accordingly, in some respects, the luer connector 710 can operate in the same or similar manner as compared to the luer connector 10 described above. As illustrated in FIG. 10A, some embodiments of the assembled luer connector 710 can comprise a housing 722, a port member 724 positioned near the second end 714 of the luer connector 710, a luer tip 726 positioned near the first end 712 of the luer connector 710, a shroud 728 surrounding at least a portion of the luer tip 726, and a valve member 720. As illustrated, the luer tip 726 can be integrally formed with the housing 722 or, in some embodiments, the luer tip 726 can be separately formed and attached to the housing 722 by any of the bonding or fusing techniques described in this disclosure or known in the art.

In the illustrated embodiment, the valve member 720 can comprise the luer tip 726, a valve tube 732 (also referred to as an internal member) supported within the luer tip 726, and a handle member 733. The valve tube 732 can be positioned at least partially within the opening 760 that can be formed in the luer tip 726. In some embodiments, the valve tube 732 and the housing 722 can be configured to permit the valve tube 732 to translate axially within a predetermined range relative to the housing 722 and luer tip 726 so that the valve tube 732 can move between the open and closed positions. In some embodiments, the valve tube 732 can define tabs, protrusions, or other features 735 to limit the axial displacement of the valve tube 732 away from the housing 722, so that the valve tube 732 is not inadvertently removed from the housing 722 as the valve tube 732 is being withdrawn. As such, the valve tube 732 can be moved between the opened and closed positions by manually pulling or pushing, respectively, on the handle 733 that can be integrally formed with or attached to the valve tube 732.

A generally fluid-tight sealing member 744 can be supported by the housing 722 and can be configured to seal the opening in the housing 722 through which the valve tube 732 can pass. In some embodiments, the sealing member 744 can be configured to provide a radial inward force on the outside surface of the valve tube 732 to impede the axial movement of the valve tube 732 relative to the housing 722. In some embodiments, the sealing member 744 can be configured to exert a biasing force on the valve tube 732 that biases the valve tube 732 to the closed position. The sealing member 744 can be designed so that a magnitude of the radial inward force is sufficient to prevent the valve member 720 from inadvertently opening from the closed position. Additionally, the sealing member 744 can be configured to substantially prevent any fluid or medicament from flowing out of the opening formed in the housing 722 through which the valve tube 732 can pass. In some embodiments, the valve tube 732, the seal 744, and/or the housing 722 can be configured to define detents, stops, or other features to bias the valve member 720 to remain in predetermined axial positions relative to the housing 722.

Figure 11A:
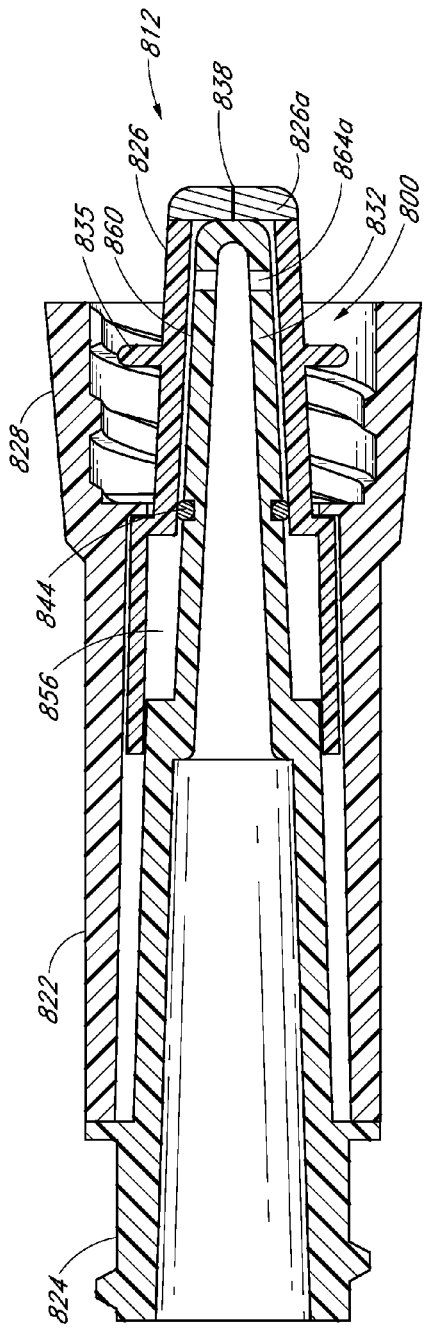
FIG. 11A is a cross-sectional view of another embodiment of a luer connector in a closed position.
Figure 11B:
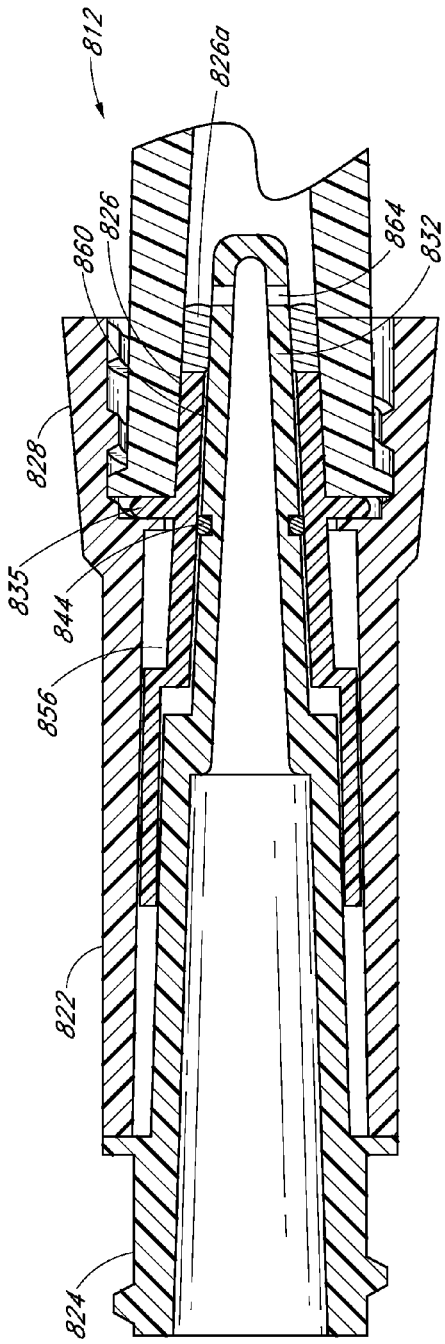
FIG. 11B is a cross-sectional view of the embodiment of the luer connector shown in FIG. 11A in an open position.

Referring now to FIGS. 11A-11B, another embodiment of a closeable luer connector 810 will be described. In some embodiments, the luer connector 810 can have or be made from any of the components, features, materials, sizes, geometries, details, or configurations of any of the other luer connectors disclosed herein. FIG. 11A is a cross-sectional view of the luer connector 810, showing the luer connector 810 in a closed position so that fluid is generally prevented from flowing through the luer connector 810. FIG. 11B is a cross-sectional view of the luer connector 810, showing the luer connector 810 in an open position so that fluid is generally permitted to flow through the luer connector 810. As will be described, in some embodiments, the luer connector 810 can be configured so that the valve member 820 of the luer connector 810 can be automatically changed between an open and a closed position. The flow of fluid or medicament through the luer connector 810 is represented by arrows in FIG. 11B. When the valve tube 832 (also referred to as an internal member) of the luer connector 810 is in the open position, fluid can be generally permitted to flow through the luer connector 810. Similarly, when the valve tube 832 is in a closed position, fluid can be generally prevented from flowing through the luer connector 810. As with any embodiment of the luer connector described herein, a perfect seal by the valve member is not required, although such a seal may be preferred in some embodiments.

In some embodiments, the luer connector 810 can be the same or similar to the luer connector 10 described above, except for or in addition to the features and components illustrated in FIGS. 11A and 11B and/or described below. Accordingly, in some respects, the luer connector 810 can operate in the same or similar manner as compared to the luer connector 10 described above. As illustrated in FIG. 11A, some embodiments of the assembled luer connector 810 can comprise a housing 822, a port member 824 positioned near the second end 814 of the luer connector 810, a luer tip 826 positioned near the first end 812 of the luer connector 810, a shroud 828 surrounding at least a portion of the luer tip 826, and a valve member 820. As illustrated, the valve tube 832 can be integrally formed with the port member 824 or, in some embodiments, the valve tube 832 can be separately formed and attached to the port member 824 by any of the bonding or fusing techniques described in this disclosure or known in the art.

In the illustrated embodiment, the valve member 820 can comprise the luer tip 826 and the valve tube 832 supported within the luer tip 826. The valve tube 832 can be positioned at least partially within the opening 860 that can be formed in the luer tip 826. In some embodiments, the luer tip 826 and the housing 822 can be configured to permit the luer tip 826 to translate axially within a predetermined range relative to the housing 822 and valve tube 832 so that the valve member 820 can move between the open and closed positions. In some embodiments, the luer tip 826 can define tabs, protrusions, or other features 835 to engage the end portion of the female connector 76 so that luer tip 826 can be retracted when the female connector 76 is threadedly engaged with the luer connector 810, as will be described below. As will be described, the luer tip 826 can be moved between the opened and closed positions by threadedly engaging or disengaging, respectively, a female connector 76 with the luer connector 810.

A generally fluid-tight sealing member 844 can be supported by the valve tube 832 and can be configured to seal the opening 860 between the outside surface of the valve tube 832 and the inside surface of the luer tip 826 so that fluid is generally prevented from flowing into the chamber 856 and inside the housing 822. In some embodiments, the luer tip 826 can be configured to be biased toward a closed position such that, as the female connector 76 is removed from the luer connector 810, the luer tip 826 automatically returns to the closed position.

With reference to FIG. 11B, as the male luer connector 810 and female connector 76 move towards each other into threaded engagement, the inside surface 86 of the female connector 76 can contact the outside surface of the luer tip 826 or the end portion of the female connector 76 can contact the tabs 835 formed on the outside surface of the luer tip 826. This can cause a fluid tight seal between the inside surface 86 of the female connector 76 and the outside surface of the luer tip 826. As the male luer connector 810 and female connector 76 move further into threaded engagement, the contact force between the female connector 76 and the luer tip 826 can force the luer tip 826 to retract so that the pliable end portion 826a of the luer tip 826 is stretched around the valve tube 832 and the opening or slit 838 in the pliable end portion 826a of the luer tip 826 is caused to be opened, thus exposing the openings 864a in the valve tube 832 and allowing fluid to flow into the female connector 76. As the female connector 76 is removed from the luer connector 810, the luer tip 826 preferably returns to its closed position.

Any features of the embodiments shown and/or described in the Figures that have not been expressly described in this text, such as distances, proportions of components, etc. are also intended to form part of this disclosure. Additionally, although this invention has been disclosed in the context of various embodiments, features, aspects, and examples, it will be understood by those skilled in the art that the present invention extends beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. Thus, it is intended that the scope of the present invention herein disclosed should not be limited by the particular disclosed embodiments described above.

The following is claimed:

1. A closed male luer connector comprising:
   a housing having a hollow bore, a first end, and a second end;
   a male luer tip of the closed male luer connector supported by the housing and configured to rotate with respect to the housing, the male luer tip having a first open end and a passageway through the male luer tip in fluid communication with the first open end; and
   a substantially rigid internal member extending into the passageway of the male luer tip toward the first open end of the male luer tip;
   wherein:
   at least one of the male luer tip and the internal member is axially moveable between a first position and a second position relative to the other of the male luer tip and the internal member;
   the male luer tip and the internal member cooperate such that rotation of the male luer tip in a first direction relative to the housing increases an axial displacement between the first open end of the male luer tip and an end portion of the internal member;
   in the first position, the end portion of the internal member provides a substantially fluid-tight seal with respect to the first open end of the male luer tip so as to substantially prevent a flow of fluid through the male luer tip; and in the second position, the end portion of the internal member is spaced apart from the first open end so that fluid is permitted to flow through the first open end of the male luer tip.

2. The luer connector of claim 1, wherein the male luer tip is configured to rotate in a first direction with respect to the housing as a female connector is threadedly connected to the luer connector.

3. The luer connector of claim 1, wherein the male luer tip and the internal member cooperate such that rotation of the male luer tip in a second direction relative to the housing decreases the axial displacement between the first open end of the male luer tip and the end portion of the internal member.

4. The luer connector of claim 1, wherein the internal member is axially moveable relative to the male luer tip.

5. The luer connector of claim 1, wherein the internal member comprises an axial opening through at least a portion of the internal member, the axial opening being in fluid communication with the hollow bore of the housing and being configured to permit fluid to flow through the internal member.

6. The luer connector of claim 1, wherein the internal member has a solid cross-section along at least a substantial portion of the length thereof such that at least a substantial amount of fluid flowing through the luer connector is required to flow around an outside surface of the internal member.

7. The luer connector of claim 1, further comprising a chamber within the housing, the chamber being configured produce a change in volume as at least one of the male luer tip and the internal member axially moves between the first position and the second position relative to the other of the male luer tip and the internal member, and wherein the volume of the chamber is larger when the male luer tip and the internal member are in the first position.

8. The luer connector of claim 1, wherein the internal member comprises a helical or angled surface, the helical or angled surface configured to cooperate with the male luer tip and to cause the change in axial displacement between the male luer tip and the internal member as the male luer tip is rotated.

9. The luer connector of claim 1, further comprising a resilient member configured to bias the male luer tip and the internal member toward the first position.

10. The luer connector of claim 1, wherein the male luer tip has a conically shaped outside surface.

11. The luer connector of claim 1, wherein an opening in the first open end of the male luer tip and the end portion of the internal member have an ovular or other non-circular cross-sectional shape.

12. The luer connector of claim 11, wherein the opening in the first open end of the male luer tip has a tapered internal wall portion, the end portion of the internal member has a tapered external wall portion that cooperates with the internal wall portion of the male luer tip, the male luer tip and the internal member being configured such that relative rotation between the male luer tip and the internal member causes axial displacement between the male luer tip and the internal member.

13. A closed male luer connector comprising:
a housing having a hollow bore, a first end, and a second end;
a male luer tip of the closed male luer connector supported by the housing and configured to axially move with respect to the housing, the male luer tip having a first open end and a passageway through the male luer tip in fluid communication with the first open end; and
a substantially rigid internal member extending into the passageway of the male luer tip toward the first open end of the male luer tip;
wherein:
the male luer tip is axially moveable between a first position and a second position relative to the internal member;
in the first position, an end portion of the internal member provides a substantially fluid-tight seal with respect to the first open end of the male luer tip so as to substantially prevent a flow of fluid through the male luer tip; and
in the second position, the end portion of the internal member is spaced apart from the first open end so that fluid is permitted to flow through the first open end of the male luer tip.

14. The luer connector of claim 13, wherein the male luer tip is configured to axially move from the first position to the second position as a female connector is threadedly connected to the luer connector.

15. The luer connector of claim 13, wherein the internal member has a solid cross-section along at least a substantial portion of the length thereof such that at least a substantial amount of fluid flowing through the luer connector is required to flow around an outside surface of the internal member.

16. The luer connector of claim 13, wherein the internal member comprises an axial opening through at least a portion of the internal member, the axial opening being in fluid communication with the hollow bore of the housing and being configured to permit fluid to flow through the internal member.

17. The luer connector of claim 13, further comprising a resilient member configured to bias the male luer tip toward the first position.

18. The luer connector of claim 13, wherein the male luer tip has a conically shaped outside surface.

* * * * *